(12) United States Patent
Fischer et al.

(10) Patent No.: US 6,914,225 B2
(45) Date of Patent: Jul. 5, 2005

(54) APPARATUS AND METHODS FOR SINGLE SHEET FORMING USING INDUCTION HEATING

(75) Inventors: John R. Fischer, Winthrop, WA (US);
Marc R. Matsen, Seattle, WA (US);
Dwayne C. Joseph, Renton, WA (US);
Larry D. Hefti, Auburn, WA (US);
Ronald W. Brown, Des Moines, WA (US)

(73) Assignee: The Boeing Company, Chicago, IL (US)

( * ) Notice: Subject to any disclaimer, the term of this patent is extended or adjusted under 35 U.S.C. 154(b) by 21 days.

(21) Appl. No.: 10/464,796

(22) Filed: Jun. 18, 2003

(65) Prior Publication Data

US 2004/0256383 A1 Dec. 23, 2004

(51) Int. Cl.[7] .................................................. H05B 6/10
(52) U.S. Cl. .................... 219/634; 219/635; 219/659
(58) Field of Search .............................. 219/600–604, 219/615–618, 659–683, 673, 676, 635, 645, 647, 649; 218/159; 228/265, 157

(56) References Cited

U.S. PATENT DOCUMENTS

| | | |
|---|---|---|
| 3,340,101 A | 9/1967 | Fields, Jr. et al. |
| 3,444,275 A | 5/1969 | Willett |
| 3,466,726 A | 9/1969 | Savolainen |
| 3,529,458 A | 9/1970 | Butler et al. |
| 3,547,751 A | 12/1970 | Morgan |
| 3,595,060 A | 7/1971 | Hundy |
| 3,605,477 A | 9/1971 | Carlson |
| 3,890,819 A | 6/1975 | DeLuca |
| 3,895,436 A | 7/1975 | Summers et al. |
| 3,920,175 A | 11/1975 | Hamilton et al. |
| 3,924,793 A | 12/1975 | Summers et al. |
| 3,927,817 A | 12/1975 | Hamilton et al. |
| 3,934,441 A | 1/1976 | Hamilton et al. |
| 3,974,673 A | 8/1976 | Fosness et al. |
| 3,996,019 A | 12/1976 | Cogan |
| 4,111,024 A | 9/1978 | Dahlman et al. |

(Continued)

OTHER PUBLICATIONS

Border, J. and R. Salas, *"Induction Heated Joining of Thermoplastic Composites Without Metal Susceptors,"* 34th *International SAMPE Symposium*, May 8–11, 1989 (pp. 2569–2578).

Sumida, A., K. Ono, and Y. Kawazu, *"Pan Based High Modules Graphitized Carbon Fiber Torayce M60J"*, 34th *International SAMPE Symposium*, May 8–11, 1989 (pp 2579–2589).

*Primary Examiner*—Tu Hoang
(74) *Attorney, Agent, or Firm*—Harness Dickey & Pierce P.L.C.

(57) ABSTRACT

Apparatus and methods for single sheet forming using induction heating include a pair of dies defining a die cavity for containing a workpiece, which is inductively heated by an oscillating magnetic field within the die cavity. A susceptor is positioned between the workpiece and one die surface defined by one of the dies. The susceptor is capable of coupling with the oscillating magnetic field to induce a current within the susceptor to heat the susceptor. The susceptor transfers heat to the workpiece. An inlet for pressurized forming fluid injects the fluid between the susceptor and the workpiece to form the workpiece into direct contact with a forming surface defined by one of the dies. The susceptor may be electrically connected to the workpiece to inhibit electrical arcing from the susceptor to adjacent electrically conductive components when current is induced in the susceptor. The apparatus may further include a seal frame that releasably engages the workpiece to form a pressurizing cavity between the susceptor and the workpiece. The inlet injects the fluid into the pressurizing cavity to develop and apply forming pressure to the workpiece.

39 Claims, 15 Drawing Sheets

U.S. PATENT DOCUMENTS

| | | |
|---|---|---|
| 4,141,484 A | 2/1979 | Hamilton et al. |
| 4,145,903 A | 3/1979 | Leach et al. |
| 4,188,811 A | 2/1980 | Brimm |
| 4,217,397 A | 8/1980 | Hayase et al. |
| 4,233,829 A | 11/1980 | Hamilton et al. |
| 4,233,831 A | 11/1980 | Hamilton et al. |
| 4,263,375 A | 4/1981 | Elrod |
| 4,269,053 A | 5/1981 | Agrawal et al. |
| 4,288,021 A | 9/1981 | Leodolter |
| 4,304,821 A | 12/1981 | Hayase et al. |
| 4,306,436 A | 12/1981 | Schulz et al. |
| 4,331,284 A | 5/1982 | Schulz et al. |
| 4,351,470 A | 9/1982 | Swadling et al. |
| 4,352,280 A | 10/1982 | Ghosh |
| 4,354,369 A | 10/1982 | Hamilton |
| 4,361,262 A | 11/1982 | Israeli |
| 4,381,657 A | 5/1983 | Hamilton et al. |
| 4,426,032 A | 1/1984 | Leodolter |
| 4,474,044 A | 10/1984 | Leistner et al. |
| 4,502,309 A | 3/1985 | Hamilton et al. |
| 4,563,145 A | 1/1986 | De Meij |
| 4,584,860 A | 4/1986 | Leonard |
| 4,603,089 A | 7/1986 | Bampton |
| 4,603,808 A | 8/1986 | Stacher |
| 4,622,445 A | 11/1986 | Matsen |
| 4,649,249 A | 3/1987 | Odor |
| 4,657,717 A | 4/1987 | Cattanach et al. |
| 4,713,953 A | 12/1987 | Yavari |
| 4,888,973 A | 12/1989 | Comley |
| 4,889,276 A | 12/1989 | Caldwell et al. |
| 4,901,552 A | 2/1990 | Ginty et al. |
| 4,951,491 A | 8/1990 | Lorenz |
| 4,984,348 A | 1/1991 | Cadwell |
| 4,988,037 A | 1/1991 | Cadwell |
| 5,047,605 A | 9/1991 | Ogden |
| 5,118,026 A | 6/1992 | Stacher |
| 5,129,248 A | 7/1992 | Yasui |
| 5,277,045 A | 1/1994 | Mahoney et al. |
| 5,309,747 A | 5/1994 | Yasui |
| 5,398,410 A | 3/1995 | Yasui et al. |
| 5,410,132 A | 4/1995 | Gregg et al. |
| 5,467,626 A | 11/1995 | Sanders |
| 5,530,227 A | 6/1996 | Matsen et al. |
| 5,638,724 A | 6/1997 | Sanders |
| 5,645,744 A | 7/1997 | Matsen et al. |
| 5,661,992 A | 9/1997 | Sanders |
| 5,683,607 A | 11/1997 | Gillespie et al. |
| 5,683,608 A | 11/1997 | Matsen et al. |
| 5,689,987 A | 11/1997 | Yasui |
| 5,692,406 A | 12/1997 | Yasui |
| 5,705,794 A | 1/1998 | Gillespie et al. |
| 5,728,309 A | 3/1998 | Matsen et al. |
| 5,737,954 A | 4/1998 | Yasui |
| 5,747,179 A | 5/1998 | Matsen et al. |
| 5,808,281 A | 9/1998 | Matsen et al. |
| 5,870,304 A | 2/1999 | Yasui |
| 5,890,285 A | 4/1999 | Pruitt et al. |
| 5,914,064 A | 6/1999 | Gillespie et al. |
| 6,087,640 A | 7/2000 | Gillespie et al. |
| 6,091,063 A | 7/2000 | Woods |
| 6,180,932 B1 | 1/2001 | Matsen et al. |
| 6,211,497 B1 | 4/2001 | Matsen et al. |
| 6,235,381 B1 | 5/2001 | Sanders et al. |
| 6,305,203 B1 | 10/2001 | Yasui |
| 6,510,601 B1 | 1/2003 | Kenney et al. |
| 6,528,771 B1 | 3/2003 | Matsen et al. |
| 6,566,635 B1 | 5/2003 | Matsen et al. |

APPARATUS AND METHODS FOR SINGLE SHEET FORMING USING INDUCTION HEATING

FIELD

The present invention relates generally to single sheet forming, and more particularly to apparatus and methods for single sheet forming using induction heating.

BACKGROUND

Superplastic forming (SPF) is a known process that involves heating and then forming workpieces through the use of dies. SPF relies on superplasticity, a material property that allows certain metals and alloys to be plastically deformed without rupture well beyond their normal limits within specific temperature ranges and strain rates.

With SPF processes, highly complex and contoured monolithic parts can be formed at a relatively low cost from such materials as titanium, steel and aluminum by reducing total part count and the assembly of details. Common applications of SPF include the manufacturing of parts for aircraft, missiles and space vehicles.

To heat the workpiece in a forming process, like SPF, hot forming, thermoforming, consolidation, or heat treatment, induction heating systems have been developed. For example, U.S. Pat. No. 5,410,132 entitled "Superplastic Forming Using Induction Heating" discloses apparatus and methods for inductively heating and superplastic forming a workpiece. U.S. Pat. No. 5,683,608 entitled "Ceramic Die for Induction Heating Work Cells" discloses a ceramic die for use in an induction heating workcell that incorporates segments of the induction coil in a spaced array within a cast ceramic or phenolic body. A peripheral compression frame, typically of phenolic, surrounds the die body and applies a compressive load to the die body through lateral and transverse reinforcing rods that are cast into the die body. Dies close to direct heat in a workpiece that is located at about the center of the induction coil. The contents of U.S. Pat. Nos. 5,410,132 and 5,683,608 are each incorporated herein by reference in their entirety as if fully set forth herein.

U.S. Pat. No. 5,728,309 entitled "Method for Achieving Thermal Uniformity in Induction Processing of Organic Matrix Composites or Metals" and U.S. Pat. No. 5,645,744 entitled "Retort for Achieving Thermal Uniformity in Induction Processing of Organic Matrix Composites or Metals", disclose methods for induction heating forming a workpiece with a ceramic die. The contents of U.S. Pat. Nos. 5,645,744 and 5,728,309 are each incorporated herein by reference in their entirety as if fully set forth herein. In each of U.S. Pat. Nos. 5,645,744 and 5,728,309, susceptors that enclose the workpiece in a heating zone are used and have a Curie Temperature that is equal to or substantially the same as the desired forming temperature for the workpiece. Temperature uniformity of the workpiece is readily achieved because the magnetic permeability of the susceptor falls to unity (i.e., the susceptor becomes paramagnetic) at the Curie Temperature, causing the temperature of the susceptors and the workpiece to be maintained at the Curie temperature. Accordingly, thermal uniformity of the heated workpiece during the forming process can be achieved irrespective of the input power fed to the induction coil by judiciously selecting the material for the susceptor. The workpiece cannot overheat if energy is used efficiently. This, in turn, allows for improved control and improved temperature uniformity in the workpiece resulting in the production of better products during the forming process.

While the advancements of induction heating systems described above have done much to reduce fabrication costs, cycle times, part and fastener counts as well as improving energy efficiency and the quality of the finished articles, among other advantages, the inventors have recognized that several issues remain. For example, the typical candidate part complexity requires a complexly shaped susceptor on the part side of the die. However, complexly shaped susceptors can be rather difficult and costly to produce. Accordingly, the inventors have recognized a need for devices and methods that eliminate the need for a complexly shaped susceptor in an induction heating systems.

In addition, the inventors have also recognized that the sealing welds presently used in induction heating systems to seal a pressurizing cavity adjacent the workpiece increase the time needed for preparation and introduce trimming (i.e., cutting of the workpiece and/or sealing welds) as a necessary step to recover the completed part. Accordingly, the inventors have recognized a need for even more efficient ways of sealing a pressurizing cavity adjacent the workpiece in induction heating systems.

SUMMARY

Apparatus and methods for single sheet forming using induction heating include a pair of dies that define a die cavity for containing a workpiece, which is inductively heated by an oscillating magnetic field within the die cavity. A susceptor is positioned between the workpiece and one die surface defined by one of the dies. The susceptor is capable of coupling with the oscillating magnetic field to induce a current within the susceptor to heat the susceptor. The susceptor transfers heat to the workpiece. An inlet for pressurized forming fluid injects the fluid between the susceptor and the workpiece to form the workpiece into direct contact with a forming surface defined by one of the dies. The susceptor may be electrically connected to the workpiece to inhibit electrical arcing from the susceptor to adjacent electrically conductive components when current is induced in the susceptor. The apparatus may further include a seal frame that releasably engages the workpiece to form a pressurizing cavity between the susceptor and the workpiece. The inlet injects the fluid into the pressurizing cavity to develop and apply forming pressure to the workpiece. A ridge may be defined by one of the dies external to the die cavity, and a corresponding relief may be defined by the other one of the dies to receive the ridge therein when the dies are closed. The ridge and the relief, when engaged with one another, inhibit heat that is radiantly transferring through a gap between the dies from transferring outwardly beyond the ridge and the relief.

Further areas of applicability of the present invention will become apparent from the detailed description provided hereinafter. It should be understood that the detailed description and specific examples, while indicating at least one exemplary embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Corresponding reference characters indicate corresponding features throughout the drawings.

DETAILED DESCRIPTION OF THE EXEMPLARY EMBODIMENTS

Figure 1:
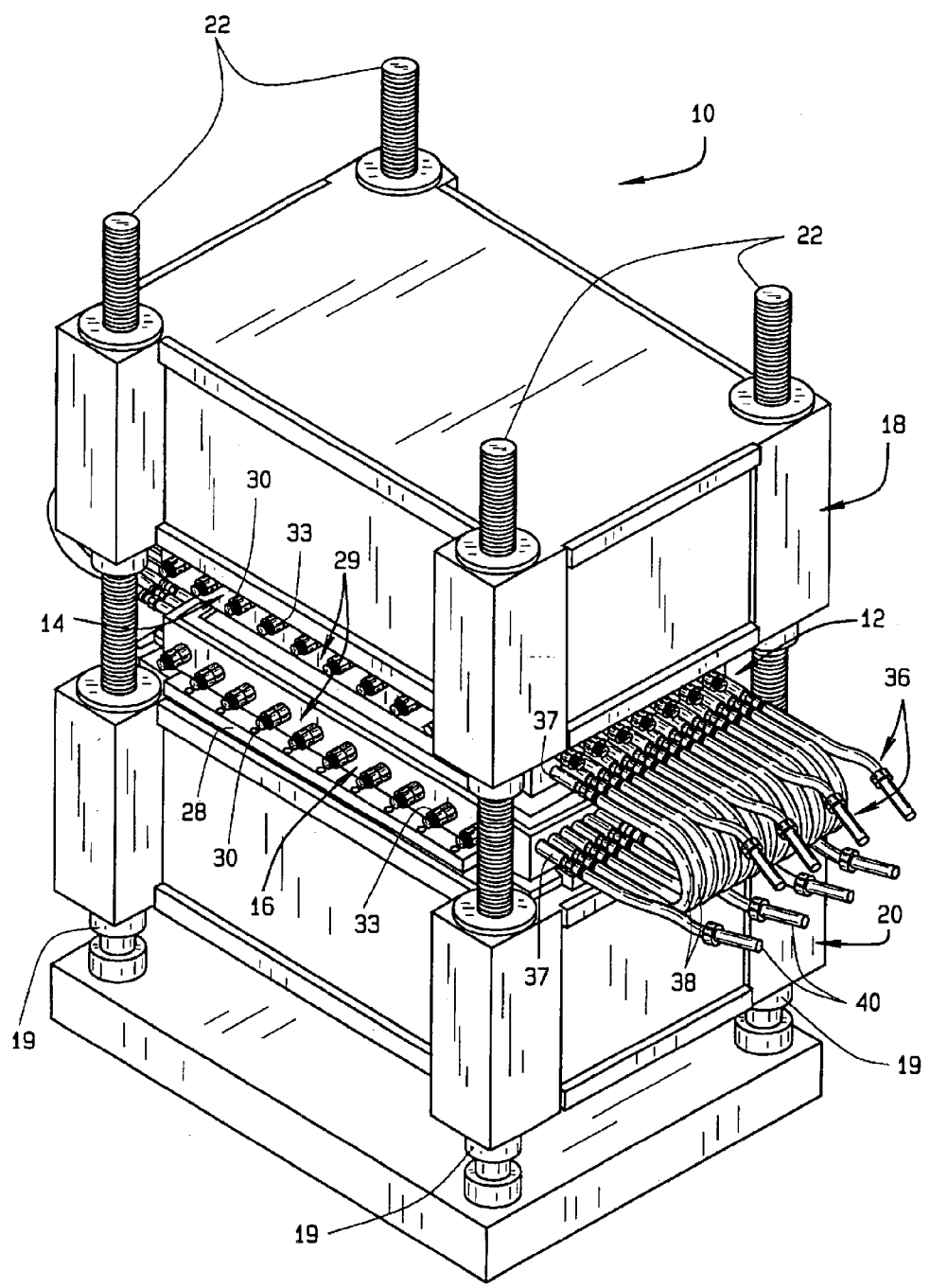
FIG. 1 is a perspective view of an induction heating forming apparatus in accordance with one embodiment of the invention.

With reference to FIG. 1 of the drawings, an induction heating forming apparatus 10 is illustrated to include a die set 12. The die set 12 may be constructed as described in U.S. Pat. No. 5,683,608.

As shown in FIG. 1, the die set 12 includes a pair of tools or dies 14 and 16, which are shown mounted within an upper strongback 18 and a lower strongback 20, respectively. The strongbacks 18 and 20 are each threaded onto four threaded column supports or jackscrews 22. The jackscrews 22 can be turned using a bellows or other actuation mechanism to move the upper and lower strongbacks 18 and 20 relative to one another.

Each strongback 18 and 20 provides a rigid, flat backing surface for its associate die 14 and 16 to keep the dies 14 and 16 dimensionally accurate and prevent them from bending and cracking during the forming operation. In one embodiment, the strongbacks 18 and 20 are capable of holding the dies 14 and 16 to a surface tolerance of about +/−0.003 inches per square foot of the forming surface in the toolbox. Such tolerances help to insure that proper part tolerances are achieved. The strongbacks 18 and 20 may be formed from steel, aluminum, or any other suitable material capable of handling the loads present during forming. In one embodiment, nonmagnetic materials are used for the strongbacks 18 and 20 to avoid any distortion to the magnetic field produced by the induction coil 36 described below. In some circumstances, the dies 14 and 16 may be strong enough themselves such that the strongbacks 18 and 20 are not necessary.

With additional reference to FIGS. 2 through 7, a forming surface 23 of the first die 14 cooperates with a die surface 24 of the second die 16 to define a die cavity 25 therebetween when the dies 14 and 16 are closed. As shown, the forming surface 23 forms the outer mold line of the workpiece 26, whereas the second die surface 24 is substantially flat.

Each of the dies 14 and 16 may be attached to its associated strongback 18 and 20 by any suitable fastening devices, such as bolts or clamps. In the illustrated embodiment of FIG. 5, the dies 14 and 16 are mounted on support plates 27 which are held in place on an associated one of the strongbacks 18 and 20 through the use of clamping bars 28. The clamping bars 28 extend around the peripheral edges of the support plates 27 and are bolted to their respective strongback 18 and 20 via fasteners (not shown).

Figure 2A:
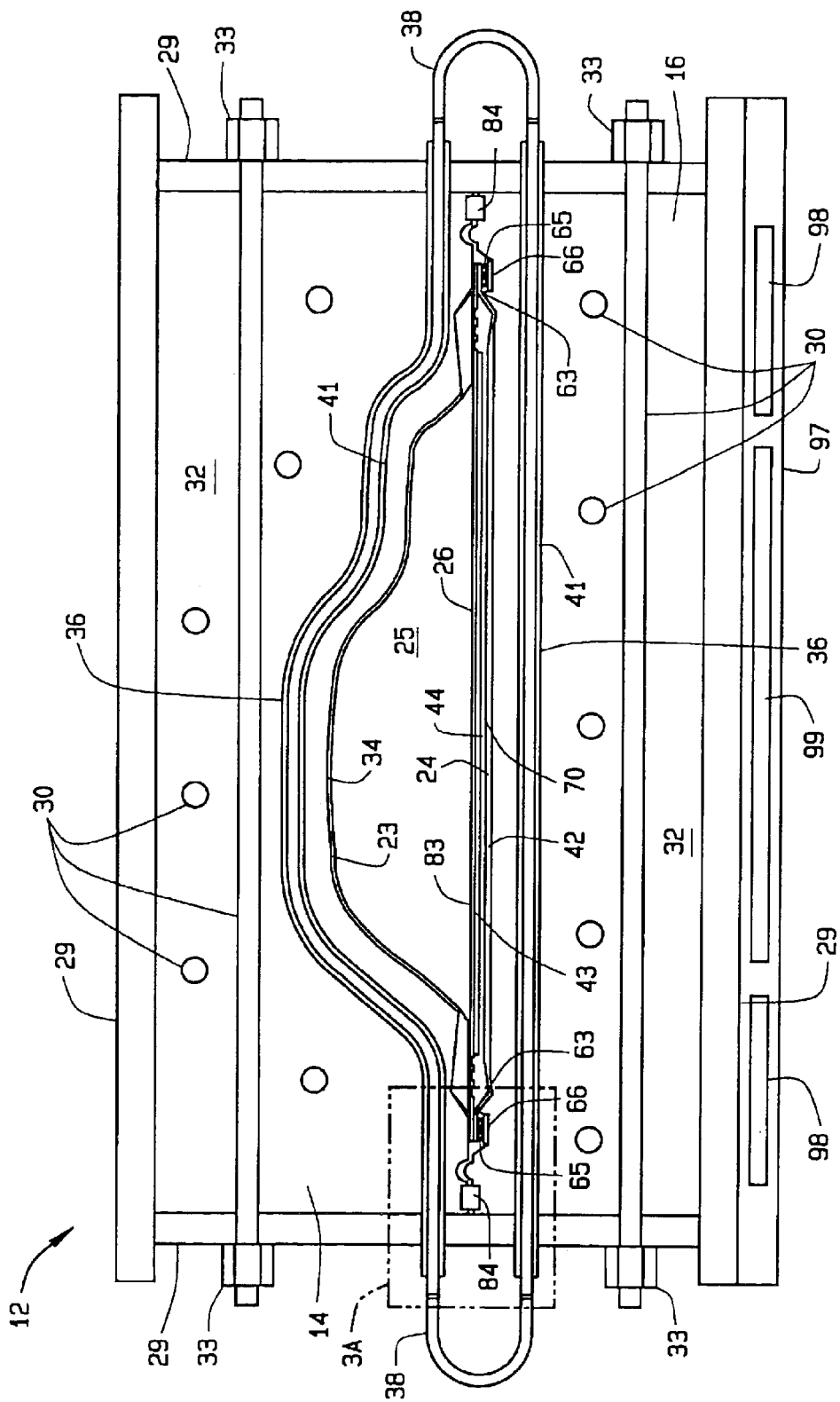
FIG. 2A is a schematic cross-sectional view of a pair of dies of the induction heating forming apparatus shown in FIG. 1 taken along a plane parallel to the length of the induction coil segments before forming the workpiece.
Figure 2B:
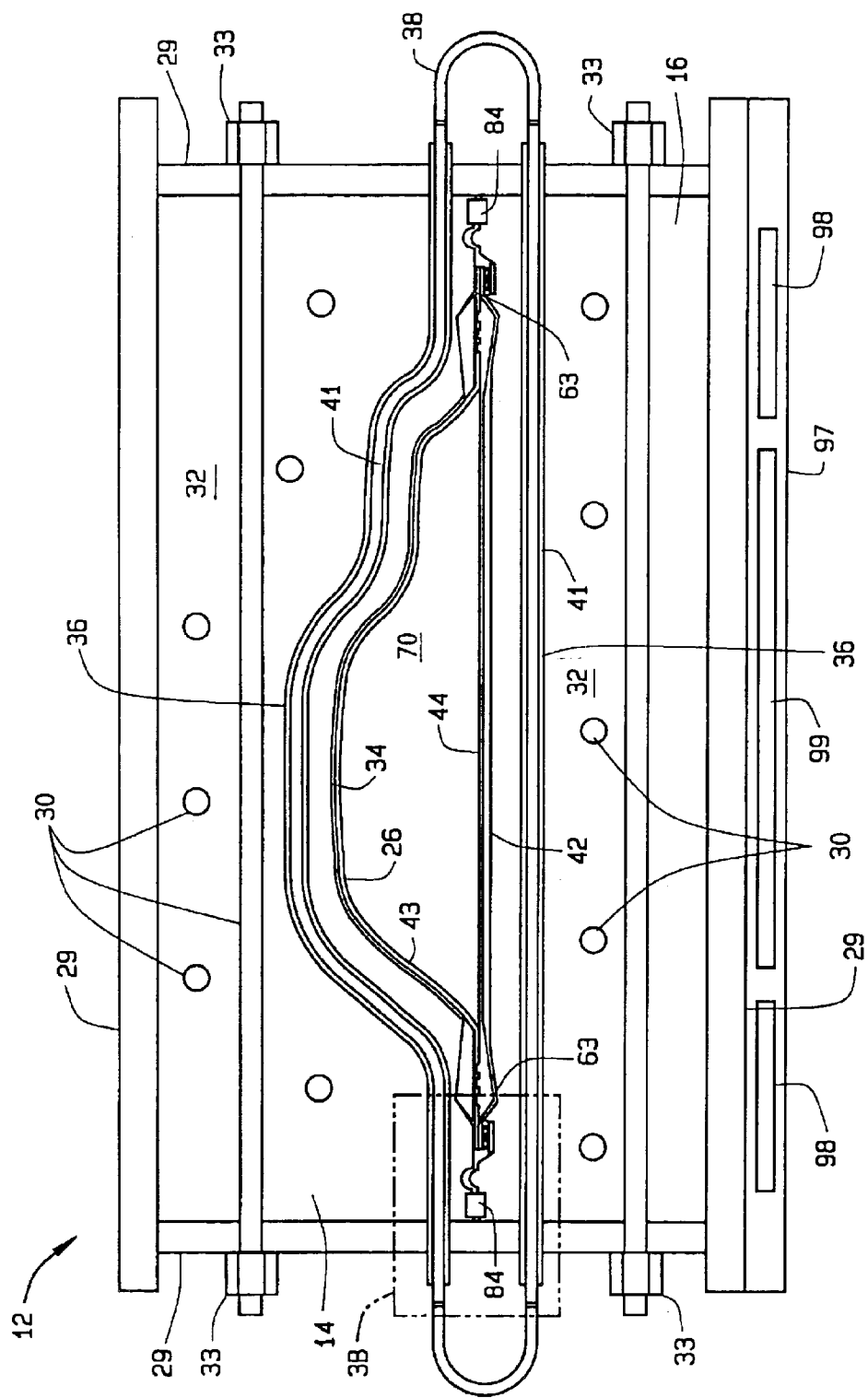
FIG. 2B is a schematic cross-sectional view of the die set shown in FIG. 2A but after forming the workpiece.

Each of the dies 14 and 16 are illustrated in FIG. 2 to include a plurality of containment walls 29, a plurality of reinforcing rods 30, and a die body 32. In the particular embodiments illustrated, the containment walls 29 are made of a material, such as phenolic, that is not susceptible to inductive heating, and which has a low coefficient of thermal expansion, good thermal shock resistance, and relatively high compression strength. Each of the containment walls 29 abuts two of the other containment walls 29 which extend transversely thereto.

The reinforcing rods 30, which are formed from fiberglass, extend both longitudinally and laterally through the containment walls 29 in a grid-like manner. In one embodiment, the reinforcing rods 30 are not electrically conductive so that they are not susceptible to induction heating. Alternatively, the reinforcing rods 30 may be formed from an electrically conductive material but be arranged such that they are not susceptible to induction heating. Tensioning nuts 33 are initially employed to apply a light clamping force to the containment walls 29 to maintain their relationship relative to one another prior to and during the formation of the die bodies 32.

Each die body 32 is made of a material (e.g., composite or ceramic material) that is not susceptible to inductive heating and that preferably has a low coefficient of thermal expansion, good thermal shock resistance, and relatively high compression strength. One exemplary material used for the die bodies 32 is a castable fused silica ceramic. One method by which the die bodies 32 may be constructed is described in U.S. Pat. No. 6,235,381 entitled "Reinforced Ceramic Structures", the contents of which is hereby incorporated by reference in its entirety as if fully set forth herein.

To increase the strength of the die bodies 32, the reinforcing rods 30 are tensioned after the die bodies 32 have been formed. Post-tensioning of the reinforcing rods 30 exerts a compressive load on the die bodies 32. Since the cast ceramic used for the die bodies 32 typically has good compressive strength but low tensile strength, this technique, which is similar to that for pre-stressing concrete, is utilized in the die construction to maintain the tolerances of the dies 14 and 16 and to prevent cracking or other damage during the use of the die set 12. The pre-applied compressive load on the die bodies 32 cancels the tensile loads that are developed during the part processing pressurization cycles. This improves performance by allowing the die bodies 32 to operate in the compressive loading range.

The forming surface 23 of the first die 14 may also include a die liner or tool insert 34. The die liner 34 is formed from a material that is not susceptible to inductive heating and which is also relatively more durable than the material used for the die body 32 of the first die 14. In this regard, the die liner 34 has at least one characteristic, such as material strength (e.g., tensile strength, shear strength, compression strength, or fatigue strength) or chemical resistance, that is different than the corresponding characteristic of the material used for the die body 32 of the first die 14. This causes the die liner 34 to be relatively more durable than the die body 32 of the first die 14. In one embodiment, the die liner 34 comprises a durable die liner as disclosed in pending U.S. patent application Ser. No. 10/011,090, filed Dec. 6, 2001, entitled "Induction Processable Ceramic Die with Durable Die Liner", the contents of which is incorporated herein by reference in its entirety as if fully set forth herein.

Figure 4:
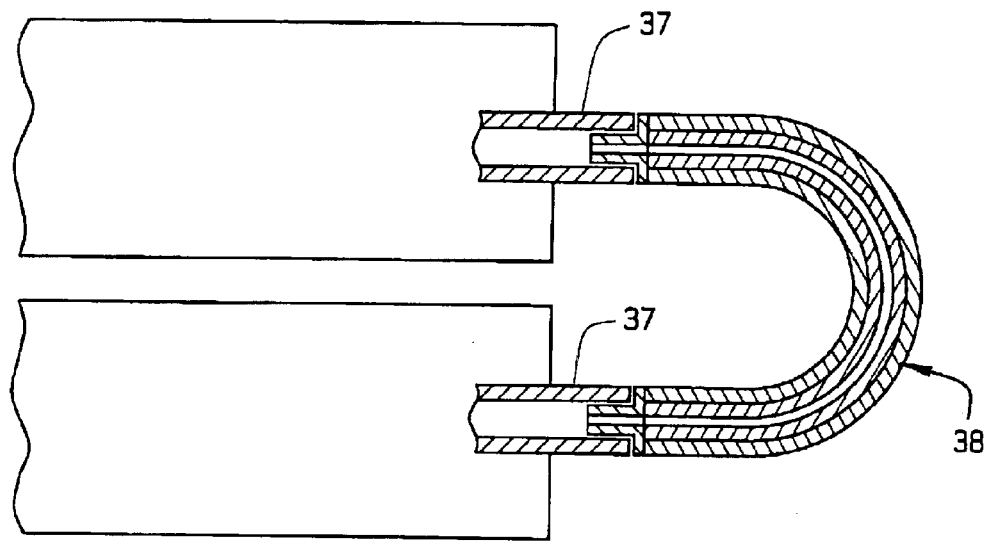
FIG. 4 is a cross-sectional view of a flexible coil connector.
Figure 7A:
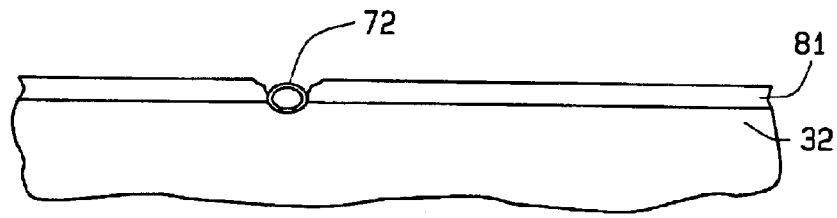
FIG. 7A is a cross-sectional view of the section 7A shown in FIG. 6.
Figure 7B:
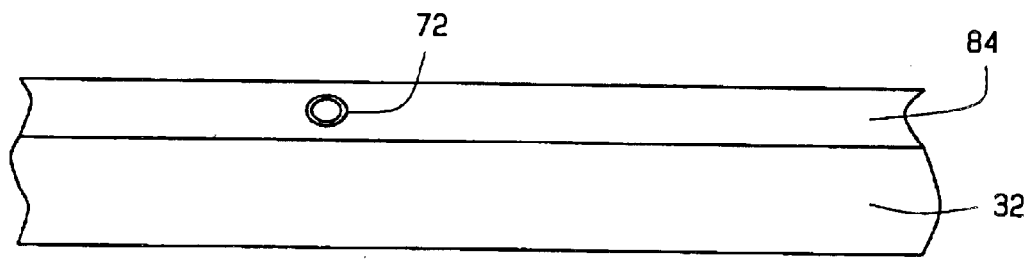
FIG. 7B is a cross-sectional view of the section 7B shown in FIG. 6.
Figure 5:
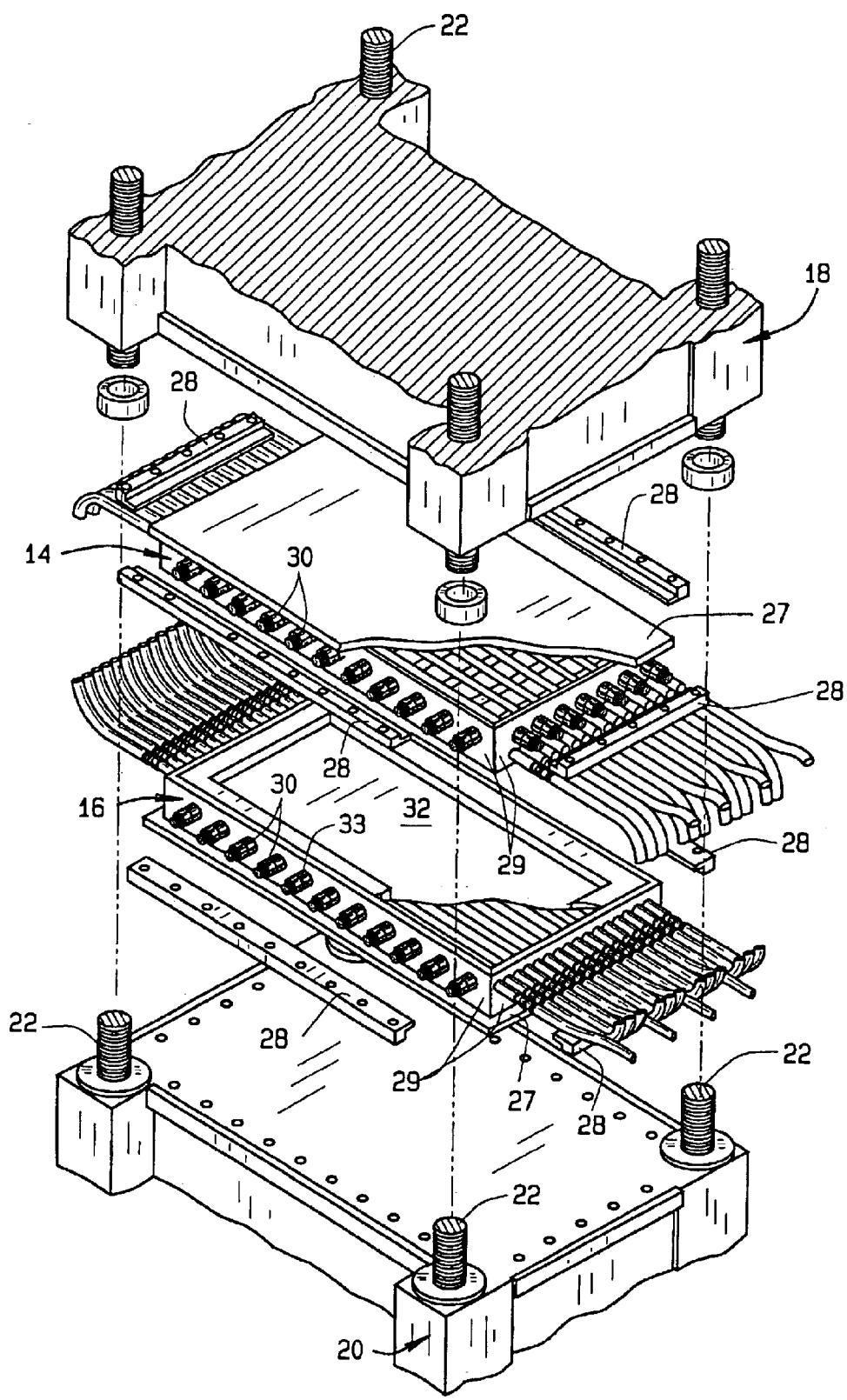
FIG. 5 is a partially exploded, partially cut away view of the induction heating forming apparatus shown in FIG. 1.

A plurality of induction coil segments extend longitudinally through the length of the dies 14 and 16, and are connected to form a solenoid coil 36 that is disposed between the reinforcing rods 30 and the die surfaces 23 and 24. In the illustrated embodiment of FIG. 1, four separate induction coil segments are used in each die half. Each induction coil segment is formed from a plurality of copper tubing sections 37 and a plurality of flexible coil connectors 38, as shown in FIG. 4. Each of the tubing sections 37 extends along the length of the die 14 and 16 in which it is disposed. In an exemplary embodiment, the tubing sections 37 are formed from a lightly drawn copper tubing that is approximately 25.4 millimeters (1.00 inch) in diameter with a wall thickness of about 1.6 millimeters (0.63 inches) and are preferably placed within the die body 32 such that they are about 19.0 millimeters (0.75 inches) away from the forming surface 23. Each of the flexible coil connectors 38 couples one of the tubing sections 37 in the die 14 to one of the tubing sections 37 in the die 16. The flexible coil connectors 38 allow the dies 14 and 16 to be opened and closed while the tubing sections 37 in the die 14 remain connected to the tubing sections 37 in the die 16. Pancake coil designs or other coil designs can also be used.

The induction coil 36 is connected to an external power source or coil driver. When actuated, the coil driver provides the induction coil 36 with an alternating electric current that causes the induction coil to produce an oscillating magnetic field within the die cavity 25. In an exemplary embodiment, the coil driver provides a 3 kilohertz (KHz) power supply frequency to the induction coil 36.

Each induction coil segment includes a lumen or inner conduit 41 therein. The lumens 41 are fluidically connected to a source of coolant by connectors 40 (FIG. 1) located at the ends of the inductive coil segments. The flow of coolant through the conduits 41 of the induction coil segments actively cools and removes excess heat from the induction coil 36. This helps ensure that the copper or other suitable material from which the induction coil 36 is made does not melt during the induction heating. The coolant flow also helps keep the ceramic dies 14 and 16 at relatively low temperatures by carrying away heat that diffuses through the ceramic. The coolant flow also allows for more rapid cooling of the workpiece 26 and the dies 14 and 16.

Forming the dies 14 and 16 as just described (i.e., from reinforced cast ceramic with an integrally cast induction coil 36) allows for significant reductions in tooling costs, safer and cooler workplaces, shorter thermal cycle times, and rapid prototyping and low volume production of new parts and assemblies. In addition, the reinforced design significantly improves the durability of the dies 14 and 16 thus extending their part fabrication capability.

In the exemplary embodiment shown in FIGS. 1 through 7, the induction heating workcell 10 includes a susceptor 42 that is positioned adjacent and between the die surface 24 of the second die 16 and only one side, i.e., the second side 43, of the workpiece 26. The susceptor 42 transfers heat at least primarily through conduction to the seal frame assembly 44 (described below), which then conducts heat to the workpiece 26. Heat transfer to the workpiece 26 from the susceptor 42 and/or the seal frame assembly 44 also occurs via convection and/or radiation.

The susceptor 42 is positioned relative to the induction coil 36 such that the susceptor 42 inductively heats when the induction coil 36 carries an alternating electric current from the coil driver. More specifically, the induction coil 36 produces electromagnetic flux in response to the oscillating electric current from the coil driver. The electromagnetic flux travels through the dies 14 and/or 16 due to the dielectric properties of the ceramic material from which the dies 14 and 16 are made. The electromagnetic flux then couples to the susceptor 42 because the high magnetic permeability of the susceptor 42 makes the susceptor 42 the lowest energy path for the electromagnetic flux to travel. The coupled oscillating electromagnetic flux causes induced currents to flow in the susceptor 42 and resistive losses occur and the susceptor 42 heats.

As shown in FIG. 2, the second die surface 24, along which the susceptor 42 is positioned, often is substantially flat or planar. The susceptor 42 is a flat sheet stock that is readily producible. Accordingly, the induction heating forming apparatus 10 does not require a complexly shaped susceptor.

Figure 8:
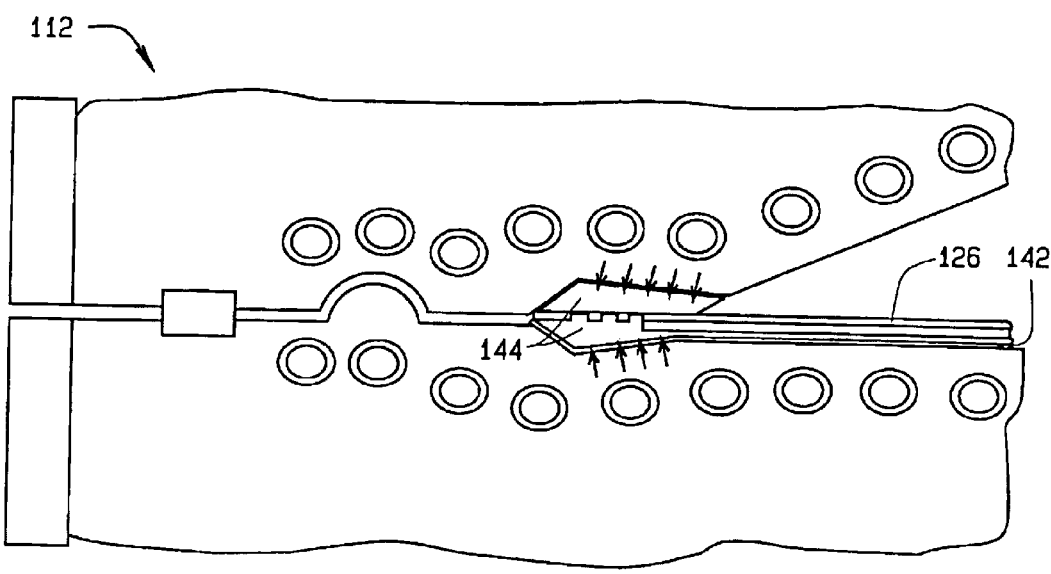
FIG. 8 is a partial cross-sectional view of a die set used in an induction heating forming apparatus according to another embodiment of the invention before forming the workpiece taken along a plane perpendicular to the length of the induction coil segments before forming the workpiece.
Figure 9:
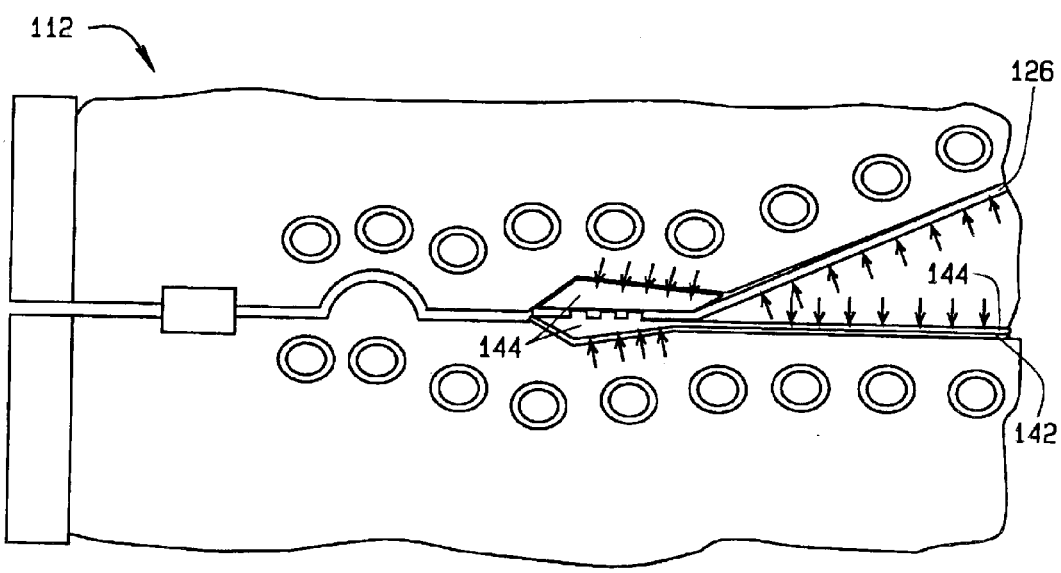
FIG. 9 is a partial cross-sectional view of the die set shown in FIG. 8 after forming the workpiece.

FIGS. 8 and 9 show a die set 112 according to another embodiment of the invention. As shown, the die set 112 also includes a susceptor 142 but does not include an enabled current path through the workpiece 126 (shown before forming in FIG. 8 and after forming in FIG. 9) or a fluid-cooled electrical connection between the workpiece 126 and the susceptor 142. Enabling a current path through a workpiece 26 with a fluid-cooled electrical connection between the workpiece 26 and the susceptor 42 is described below for the die set 12 shown in FIGS. 2, 3 and 6.

Figure 10:
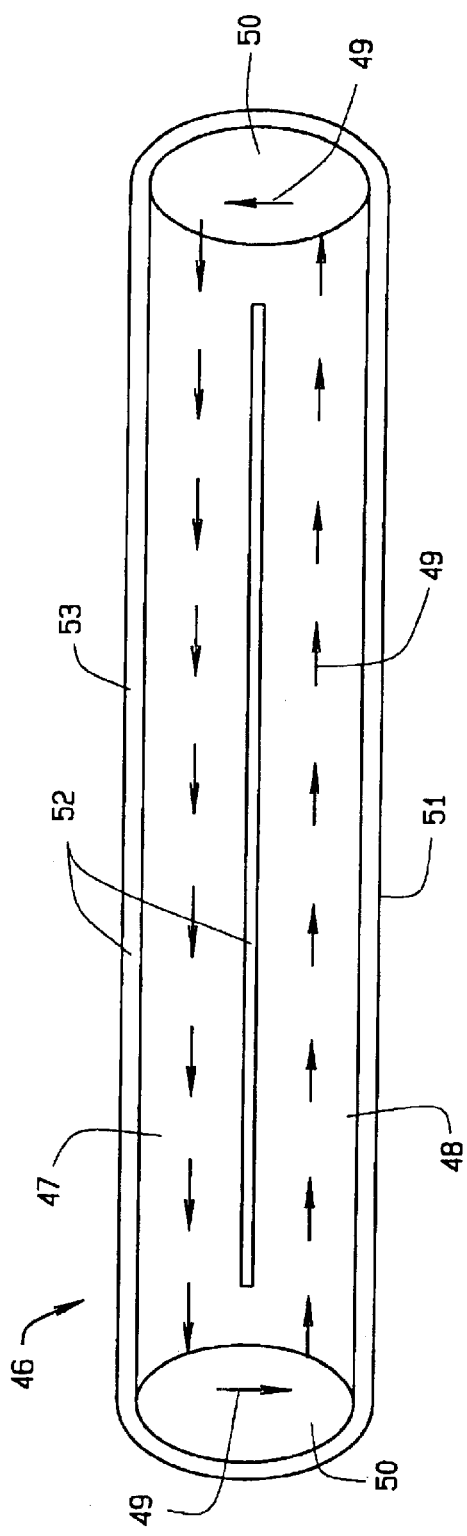
FIG. 10 is a side elevation view of a two-sheet susceptor constructed in accordance with the teachings of the invention.

As shown in FIG. 10, the susceptor 42 (FIGS. 2, 3, and 6) and/or 142 (FIGS. 8 and 9) may be formed from two sheets 47 and 48 of a material susceptible to inductive heating and which is also preferably superplastic, such as an alloy of the ferromagnetic elements iron, nickel, and cobalt. To enable an current loop within the two-sheet susceptor 46 (FIG. 10), the sheets 47 and 48 are welded or electrically connected to each other at their opposing edges which allows the current, indicated by arrows 49, to flow from one sheet to the other. Producing the two-sheet susceptor 46 involves masking the weld areas 50 and then plasma spraying or coating the outside surfaces of sheets 47 and 48 with a material 51 (e.g., a nickel aluminide, etc.) to inhibit oxidation and interaction of the sheets 47 and 48 with the ceramic dies 14 and 16 and/or the atmosphere. Next, an electrically nonconductive material 52 (e.g., an aluminum oxide, etc.) is applied between the sheets 47 and 48 and applied on the susceptor surface 53 that will be facing the workpiece (while the weld areas 50 remain masked). This coating 52 inhibits electrical arcing from one sheet to the other and/or from one sheet to adjacent electrically conductive components, such as the workpiece and the seal frame, when current is induced in the susceptor. The opposing edges of the sheets 47 and 48 are then welded to enable the current path therebetween. The weld areas 50 are subsequently plasma sprayed on the outside surface of the two-sheet susceptor 46 with the oxidation-inhibiting material 51 and the electrically nonconductive material 52 as needed.

Figure 11:
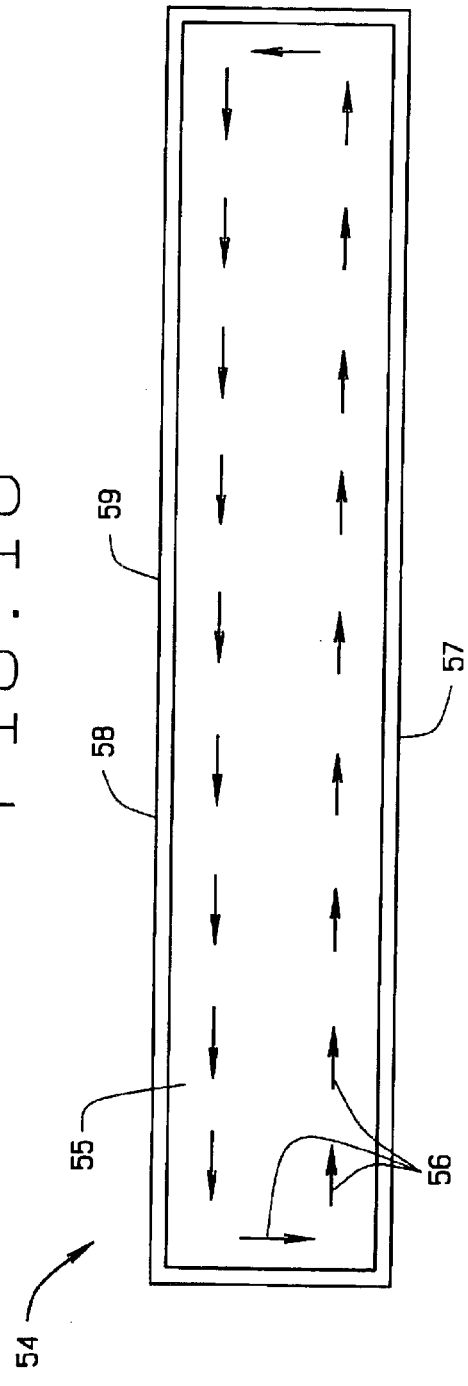
FIG. 11 is a side elevation view of a single-sheet susceptor constructed in accordance with the teachings of the invention.

As shown in FIG. 11, the susceptors 42 and/or 142 may comprise a single sheet 55 of material susceptible to inductive heating and which is also preferably superplastic, such as an alloy of the ferromagnetic elements iron, nickel, and cobalt. As shown in FIG. 11, the single sheet 55 is sufficiently thick for the induction frequency to allow a non-canceling current path to exist in the single sheet 55. Thus, the entire current loop, indicated by arrows 56, resides within the single-sheet susceptor 54. Producing the single-sheet susceptor 54 also involves plasma spraying or coating one surface of the single sheet 55 with a material 57 that inhibits oxidation and interaction of the susceptor 54 with the ceramic dies 14 and 16 and/or with the atmosphere. An electrically nonconductive material 58 is then applied to at least the susceptor surface 59 that will be facing the workpiece. This coating 58 inhibits electrical arcing from the susceptor 54 (when current is induced in the susceptor 54) to adjacent electrically conductive components, such as the workpiece and the seal frame, as in the two-sheet susceptor 46.

Figure 12A:
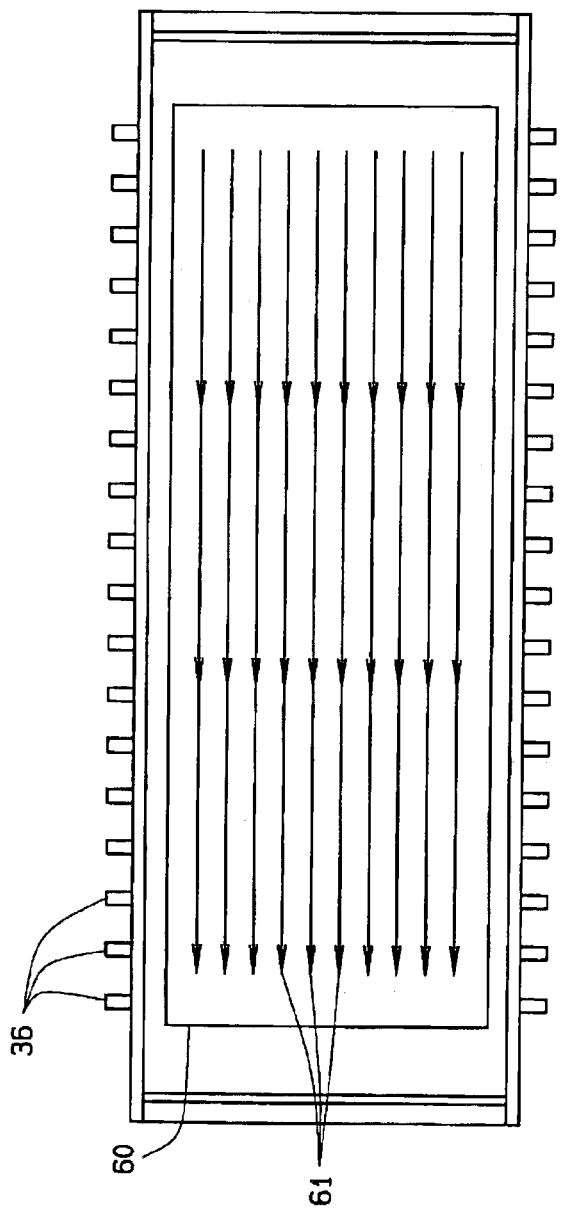
FIG. 12A is a plan view of a bottom one of the dies and a susceptor shown in FIG. 2 showing the magnetic flux lines when the susceptor is magnetic.
Figure 12B:
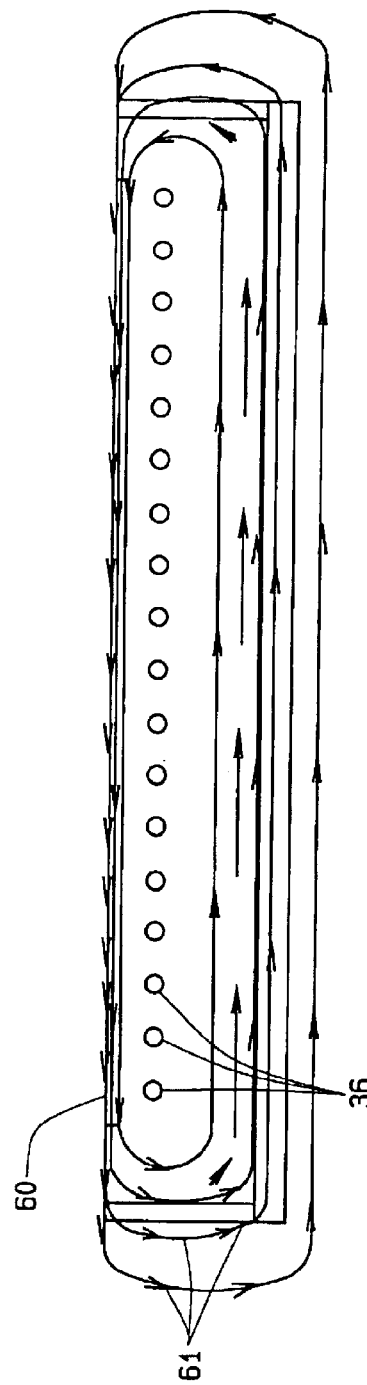
FIG. 12B is a side elevation view of the bottom die and susceptor shown in FIG. 12A.
Figure 13A:
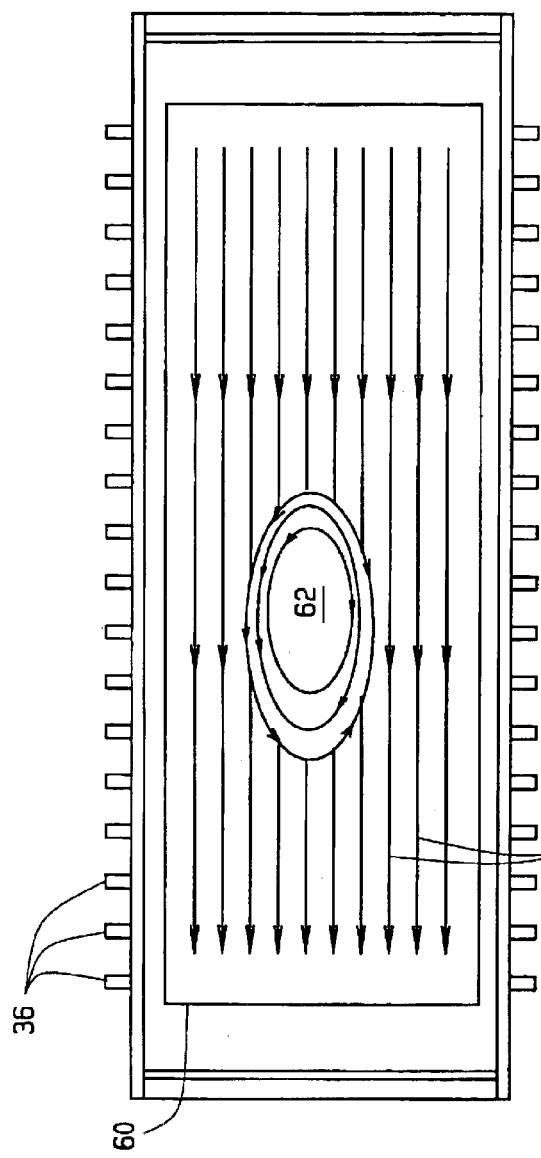
FIG. 13A is a plan view of the bottom die and the susceptor shown in FIG. 12A showing a region of magnetic impermeability in the susceptor.
Figure 13B:
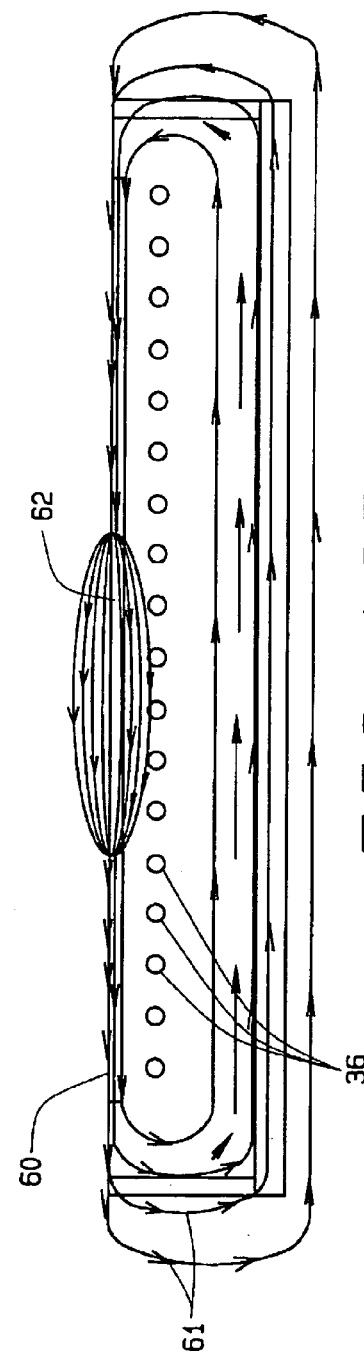
FIG. 13B is a side elevation view of the bottom die and the susceptor with the region of magnetic impermeability shown in FIG. 13A.

In some embodiments, the material composition of the susceptor is based on its Curie Temperature to facilitate temperature control at a desired processing temperature as disclosed in U.S. Pat. Nos. 5,645,744 and 5,728,309. The susceptor may be fabricated from an alloy of the ferromagnetic elements iron, nickel, and cobalt. The Curie Temperature is the temperature above which the susceptor material becomes non-magnetic. While the susceptor 60 is still magnetic, the susceptor 60 efficiently attracts and tightly houses the magnetic flux, indicated by arrows 61, generated by the induction coil 36 as shown in FIGS. 12A and 12B. During heating, the area 62 of the susceptor 60 to first reach the Curie Temperature becomes nonmagnetic or paramagnetic first. The magnetic field then distorts (see FIGS. 13A and 13B) because the magnetic flux lines 61 have a lower energy path around the hot area 62 and through the adjacent magnetic material. Also, the magnetic flux is no longer tightly contained within the thickness of the susceptor 60 as shown in FIG. 13B.

During operation, the susceptor 60 heats upon receipt of the magnetic flux from the induction coil 36 until the Curie Temperature is reached. At this point, the susceptor 60 becomes much less susceptible to induction heating because the magnetic permeability drops significantly. Induction heating above the Curie Temperature requires a substantial increase in input current over that which is required for sustained operation at the Curie Temperature since the paramagnetic phase of the susceptor 60 heats inefficiently. Accordingly, by judiciously selecting the material composition of the susceptor 60 based on its Curie Temperature, uniform temperature control throughout the susceptor 60 can be achieved.

Alternatively, temperature control may instead be achieved in some embodiments of the invention by controlling the input power that is fed to the induction coil 36 so that the desired temperature is maintained at a relatively constant level for a predetermined time while the processing of the workpiece is completed. For example, temperature control may be achieved in the manner described in U.S. Pat. No. 6,528,771 entitled "System and Method for Controlling an Induction Heating Process", the contents of which is incorporated herein by reference in their entirety as if fully set forth herein.

To inhibit electrical arcing from a susceptor to adjacent electrically conductive components when current is induced in the susceptor, some embodiments include a current path enabled through the susceptor and the workpiece. The electrical connection allows the current to flow along a preferred path that is closest to the induction coil. When only the susceptor is enabled as the current path, voltage can build-up at the interfaces connecting the components comprising the current path (i.e., the susceptor and workpiece effectively form a capacitor with charge stored in the susceptor) and arcing can occur. Enabling the current path that is closest to the induction coil 36 by electrically connecting the workpiece and susceptor significantly reduces the voltage build-up at such interfaces and eliminates, or at least significantly reduces, electrical arcing from the susceptor to electrically conductive components adjacent thereto. To further inhibit arcing from the susceptor, an electrically nonconductive (e.g., an oxide) may be applied between the susceptor and the workpiece. The electrically nonconductive material, however, should not be applied to those portions of the susceptor or the workpiece through which the electrical connection between the susceptor and the workpiece is made. By inhibiting arcing, these embodiments of the invention significantly improve processing capability of induction heating forming applications. This, in turn, leads to improved quality and reduced costs to produce the finished products. Such finished products may include unitized and monolithic structures (e.g., plates having stiffeners machined therein and/or welded thereon), automotive body panels and frames, parts for aerospace applications (e.g., monolithic heat shields, engine cowls, reinforced panels and doors, etc.), among other applications.

Figure 3A:
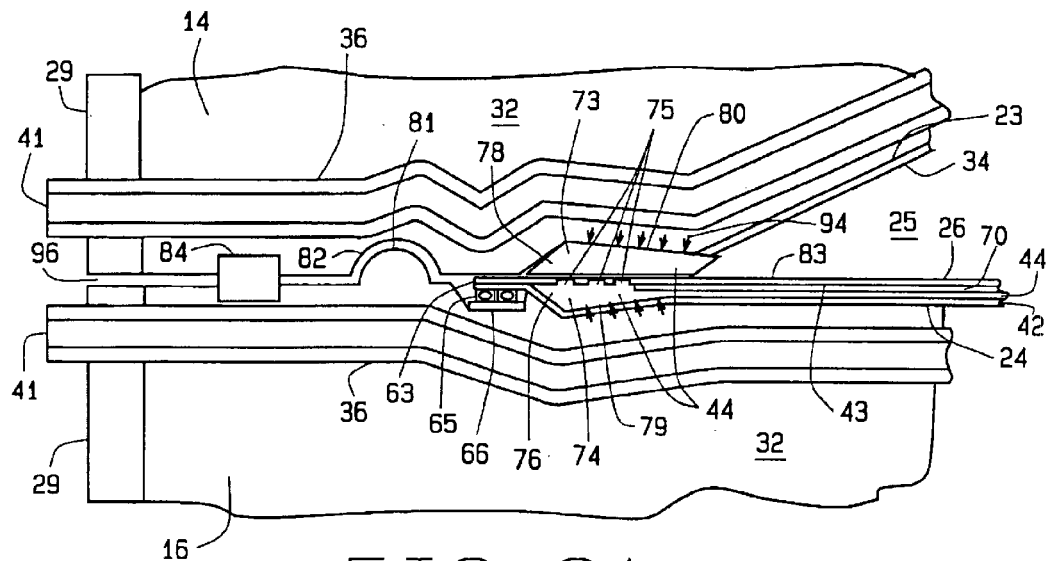
FIG. 3A is a detailed view of the section 3A shown in FIG. 2A.
Figure 3B:
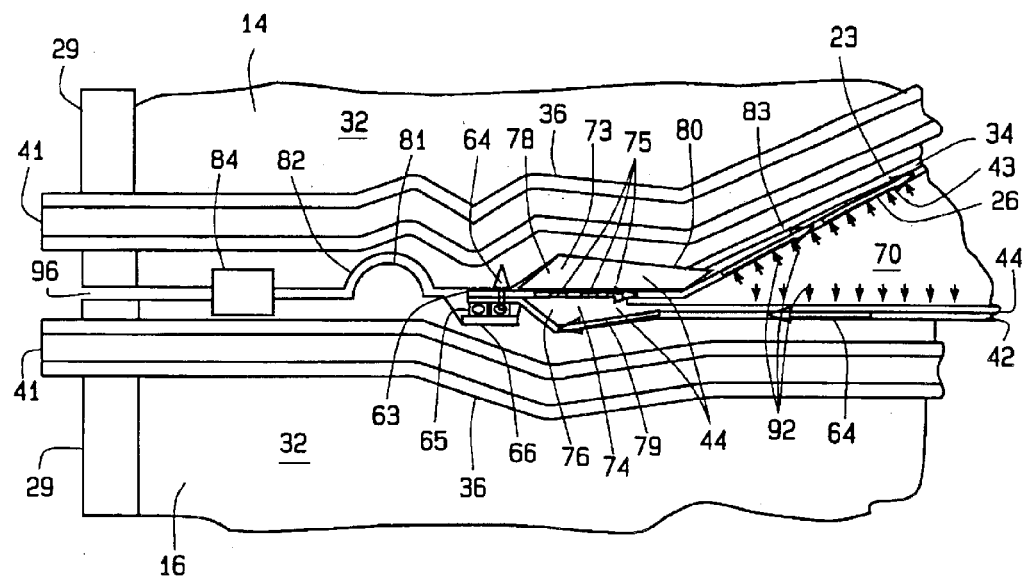
FIG. 3B is a detailed view of the section 3B shown in FIG. 2B.

In the exemplary embodiment shown in FIGS. 2 and 3, portions 63 of the susceptor 42 physically contact the workpiece 26 to establish an electrical connection therebetween. As shown in FIG. 3B, the current, indicated by arrows 64, can flow from the susceptor 42 into the workpiece 26, and vice versa. Current flowing in the workpiece contributes to its heating.

Figure 14:
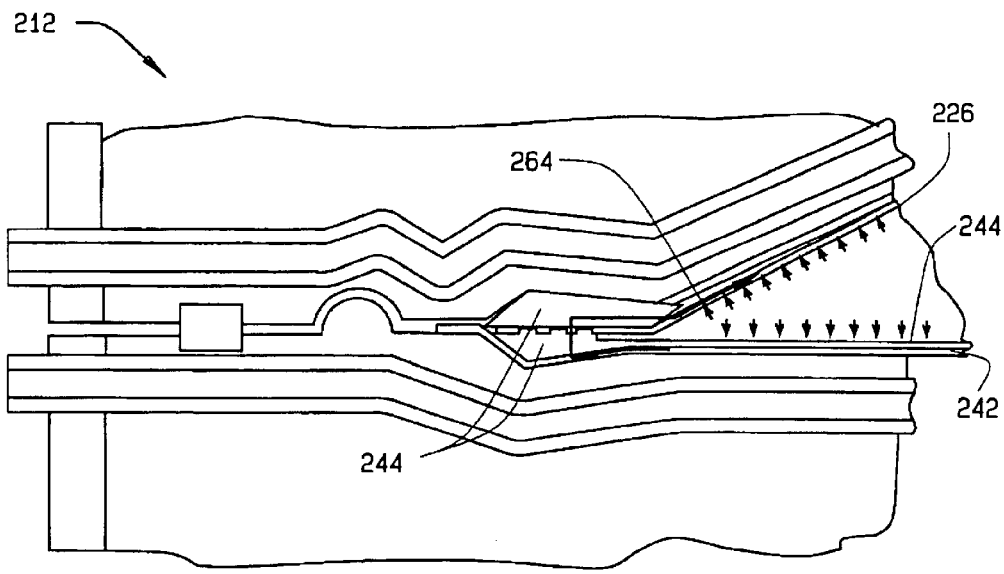
FIG. 14 is a partial cross-sectional view of a die set used in an induction heating forming apparatus according to another embodiment of the invention wherein a current path is enabled through a susceptor, a seal frame, and a workpiece.

Alternatively, an electrically conductive component may be positioned between and in physical contact with both the workpiece and the susceptor to establish the electrical connection between the workpiece and the susceptor. For example, FIG. 14 illustrates a die set 212 in which the seal frame 244 electrically connects the workpiece 226 to the susceptor 242 thus allowing the current 264 to flow between the susceptor 242 and the workpiece 226 through the seal frame 244.

Figure 6:
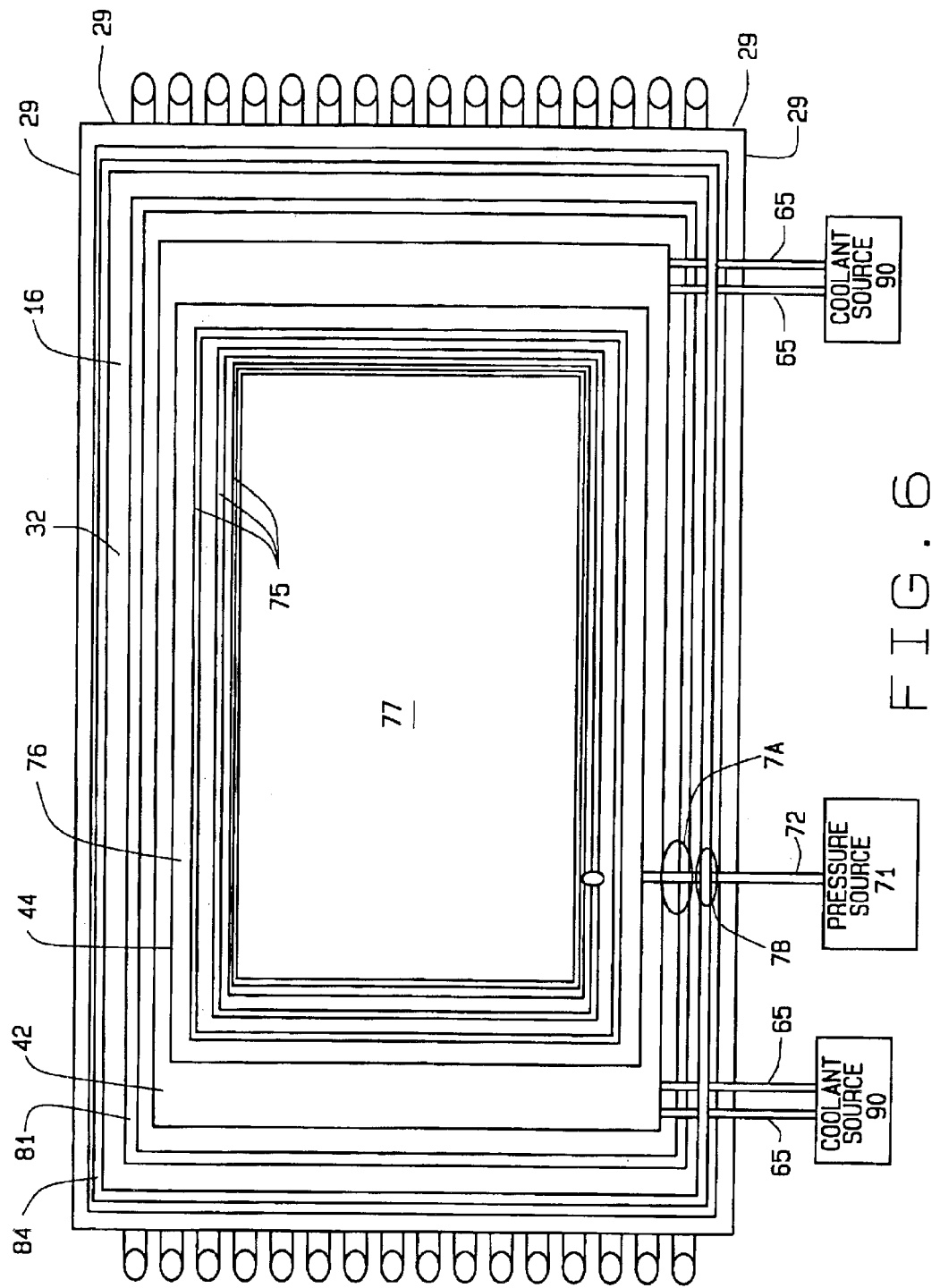
FIG. 6 is a plan view of the lower portion of the die set used in the induction heating forming apparatus shown in FIG. 1.

Optionally, the electrical connection between the workpiece and the susceptor may be actively cooled with a coolant, such as water. As shown in FIGS. 2, 3, and 6, a plurality of cooling passages or channels 65 are connected to a coolant source 90 (FIG. 6) and positioned to deliver coolant adjacent the electrical connection between the susceptor 42 and the workpiece 26. The flow of coolant through the cooling passages 65 removes excess heat from the susceptor 42 and/or the workpiece 26.

A wide range of thermally conductive materials may be used for the cooling channels 65. In one embodiment, hollow copper cooling channels 65 are used which operate like the cooling coils in the dies. See FIG. 15.

Figure 15:
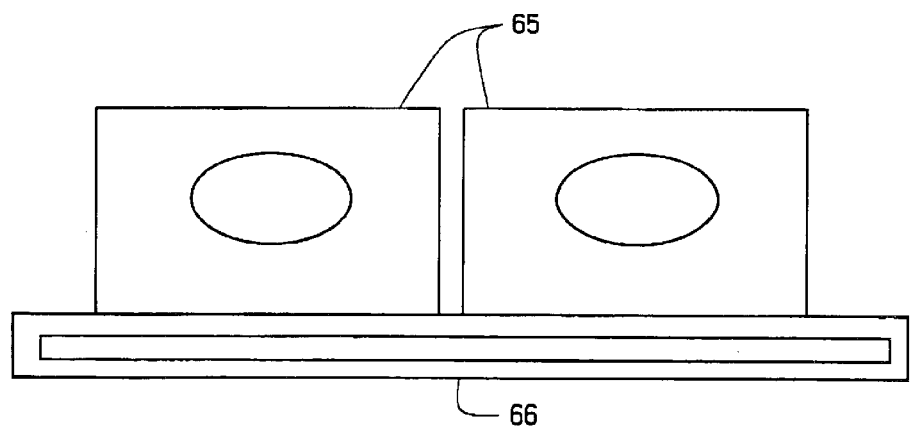
FIG. 15 is a detailed view of the coolant delivery channels shown in FIGS. 2, 3, and 16.

With further reference to FIG. 15, a pressure bladder 66 is shown positioned beneath the cooling channels 65. Although a wide range of materials may be used, the pressure bladder 66 in an exemplary embodiment is formed from 0.040 inch (0.10 centimeter) gauge corrosion-resistant stainless steel.

It should be noted that the cooling channels can also be used with a die set 312 (FIG. 16) that includes a retort or "envelope" susceptor 342 formed by a pair of susceptor sheets 368 and 369. The retort 342 may comprise a retort described in any one of U.S. Pat. Nos. 5,645,744; 5,728,309; and 6,528,771.

Figure 16:
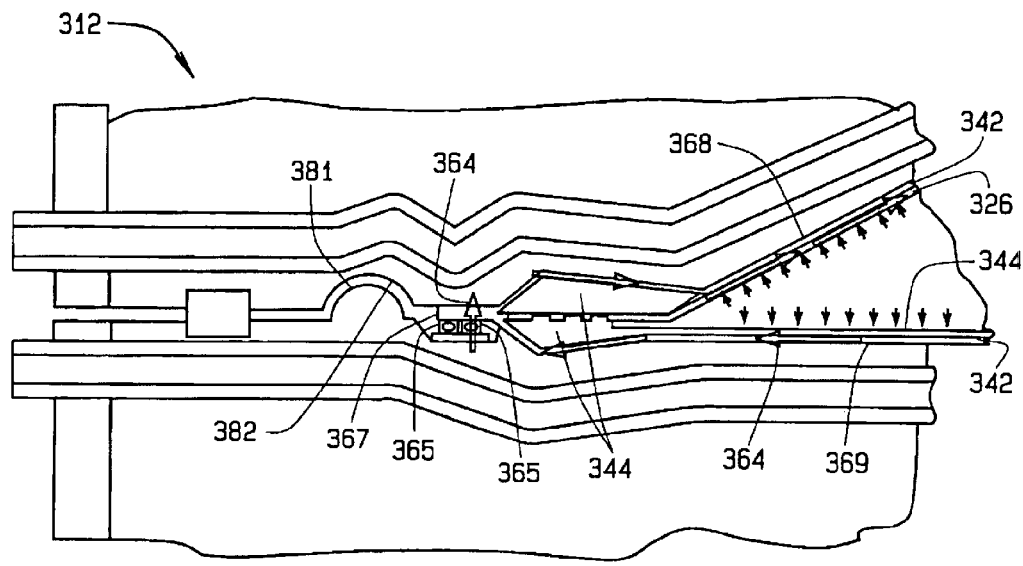
FIG. 16 is a partial cross-sectional view of a die set used in an induction heating forming apparatus according to another embodiment of the invention which includes a fluid-cooled connection at the interfaces of the two susceptor sheets of a retort taken along a plane parallel to the length of the induction coil segments after forming the workpiece.

In FIG. 16, the cooling channels 365 are used to deliver coolant adjacent the interfaces 367 between the first and second susceptor sheets 368 and 369 forming the retort 342. The current 364, after traveling through the second susceptor sheet 369, crosses the interface 367 and flows into either or both of the first susceptor sheet 368 and/or the workpiece 326. The complexly shaped susceptor sheet 368 may be formed according to the process described in pending U.S. patent application Ser. No. 10/094,494, filed Mar. 8, 2002, entitled "Smart Susceptor Having a Geometrically Complex Molding Surface", the contents of which is incorporated herein by reference in their entirety as if fully set forth herein.

Figure 17:
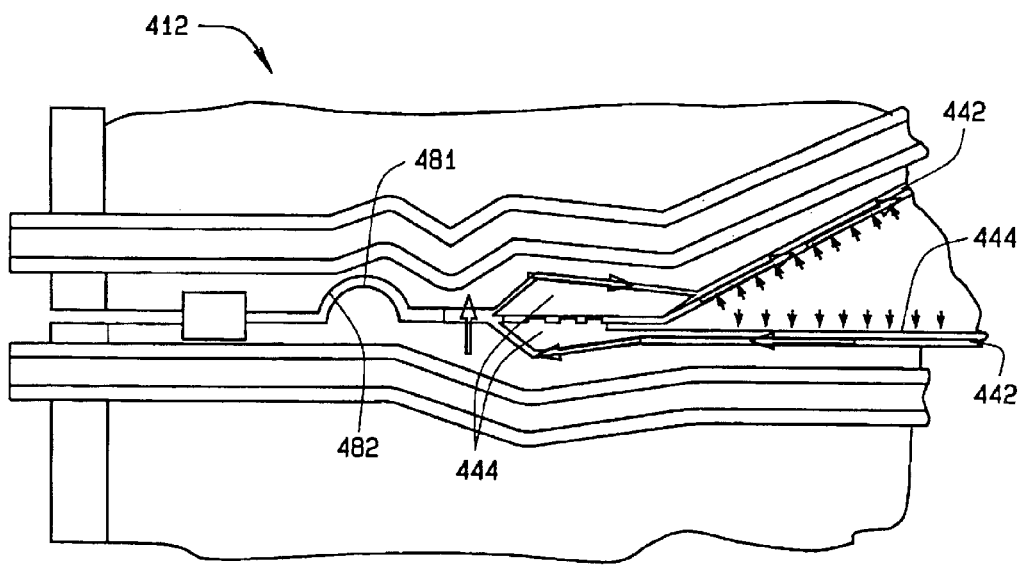
FIG. 17 is a partial cross-sectional view of a die set used in an induction heating forming apparatus according to another embodiment of the invention which includes a retort formed by a pair of susceptor sheets taken along a plane parallel to the length of the induction coil segments after forming the workpiece.
Figure 18:
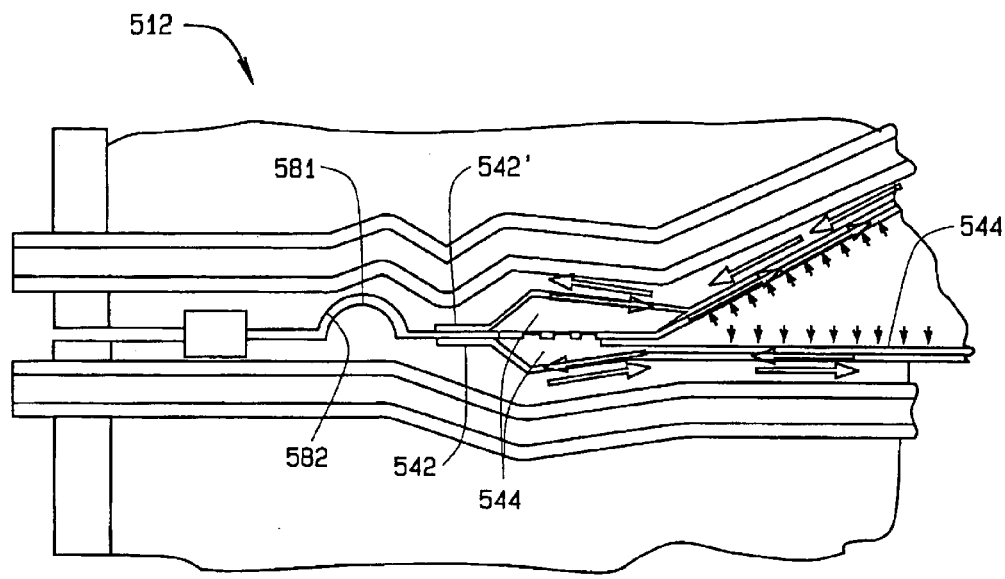
FIG. 18 is a partial cross-sectional view of a die set used in an induction heating forming apparatus according to another embodiment of the invention which includes two susceptors.

Embodiments of the invention may further include a seal frame assembly 44 (FIGS. 2 and 3), 144 (FIGS. 8 and 9), 244 (FIG. 14), 344 (FIG. 16), 444 (FIG. 17) and 544 (FIG. 18). Referring to FIGS. 2 and 3, the seal frame assembly 44 releasably engages the workpiece 26 to form a pressurizing cavity 70 between the second workpiece side 43 and the seal frame assembly 44. In each of the die set embodiments 12, 112, 212, 312, 412, 512 in which the seal frame is used, the seal frame eliminates the need for trimming or cutting of the workpiece and/or the seal frame for part removal, which is required when conventional seal welds are used. The seal frame also reduces the preparation time when compared with seal welds.

The pressurizing cavity 70 is in fluid communication with a pressure source 71 via conduit 72 (e.g., stainless steel tube, etc.). See FIG. 6. Providing the pressurizing cavity 70 with a pressurized forming fluid from the pressure source 71 allows forming pressure, indicated by arrows 92 in FIG. 3B, to be developed and applied to the second workpiece side 43 so that the workpiece 26 deforms under the pressure and is pushed into conformance with the forming surface 23 of the first die 14.

Figure 20:
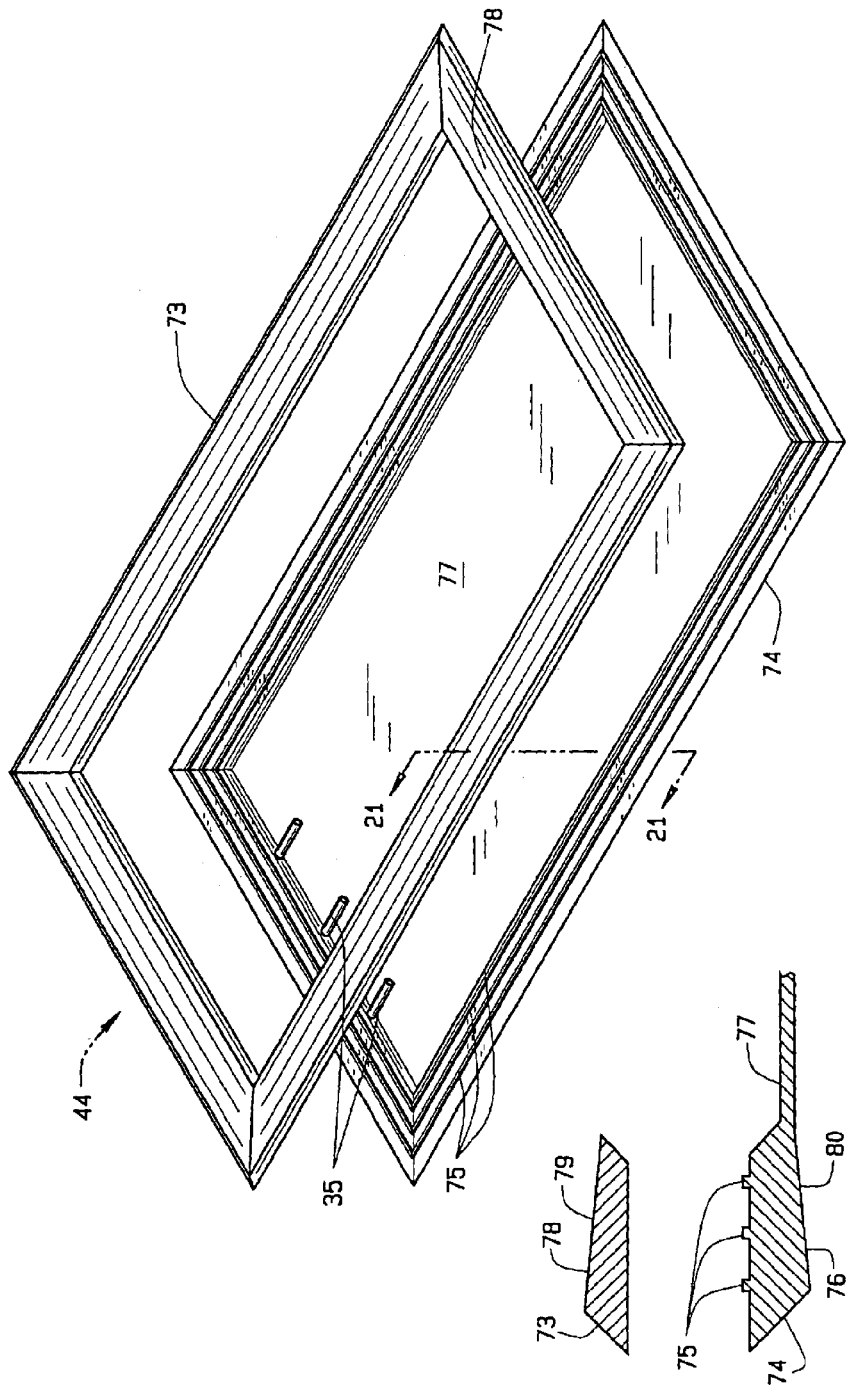
FIG. 20 is a perspective view of a seal frame according to another embodiment of the invention.
Figure 21:
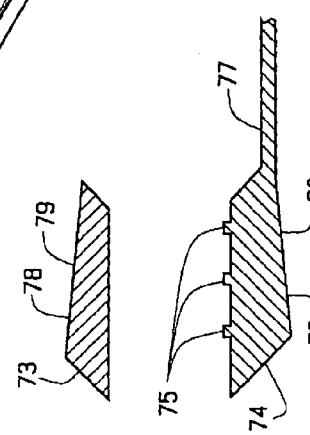
FIG. 21 is a cross-sectional view of the seal frame taken along the plane 21—21 shown in FIG. 20.

In the particular illustrated embodiment shown in FIGS. 3, 20 and 21, the seal frame assembly 44 includes first and second seal frame members 73 and 74. The seal frame assembly 44 also includes seal beads 75 that are releasably pressable into the workpiece 26 for fluidically sealing the pressurizing cavity 70. In the illustrated embodiment, the second seal frame member 74 includes three seal beads 75, however, other quantities of seal beads 75 can also be used. Moreover, either or both the first and second seal frame members 73 and 74 may include seal beads 75. In addition, a wide range of shapes may be used for the seal beads 75 including rectangular, triangular, etc. As described below, the seal beads 75 are pressed into the second workpiece side 43 when the first pressure zone 98 of pressure bladder 97 is sufficiently pressurized.

The second seal frame member 74 has a periphery 76 and a thinner, continuous medial portion 77, as shown in FIGS. 2, 3, 6, 20 and 21. The first seal frame member 73 has a periphery 78 but the middle portion has been completely removed (e.g., milled away during the machining process used to make the first seal frame member 73).

Each of the peripheral portions 76 and 78 include tapered exterior surfaces 79 and 80, respectively. This tapering helps the seal frame members 73 and 74 to retain their shape when the workpiece 26 is being heated and formed. As the workpiece 26 draws in toward the center of the die cavity 25, this tapering also causes the seal frame members 73 and 74 to become wedged more tightly together, as indicated by arrows 94 in FIG. 3A, thus helping to ensure a leak free seal.

As shown in FIG. 20, the seal frame assembly 44 may further include one or more inlets or ports 35 defined through the second seal frame member 74. In one embodiment, wires from a thermocouple or thermoelectric devices extend through the seal frame assembly 44 via the ports 35. Compression fittings can be used to fluidically seal the openings or ports 35 in the seal frame assembly 44 through which the wires of the thermocouples extend.

A wide range of materials may be used for the seal frame members 73 and 74. In one exemplary embodiment, the seal frame members 73 and 74 are machined from materials having a coefficient of thermal expansion about equal to the workpiece material and having good high temperature properties, such as titanium, stainless steel, and aluminum.

The seal frame assembly need not be limited to use with induction heating forming apparatus that include only susceptors 42, 142, or 242. For example, the seal frame can be used in conjunction with induction heating forming apparatus that inductively heat the workpiece, not with a susceptor, but by directly subjecting the workpiece to the electromagnetic flux produced by the induction coil. In addition, a seal frame assembly 344, 444 may also be used in die sets 312, 412 that include two-sheet "envelope" susceptors 344, 444 as shown in FIGS. 16 and 17. Yet another embodiment in which a seal frame assembly 544 may be used is shown in FIG. 18 which illustrates a die set 512 that includes two susceptors, a substantially flat susceptor 542 and a complexly shaped susceptor 542'. An entire current loop resides within each susceptor 542, 542' such that there is no need for an electrical connection between the susceptors 542, 542'. This, in turn, allows each susceptor 542, 542' to heat independently. The complexly shaped susceptor 542' may be formed according to the process described in pending U.S. patent application Ser. No. 10/094,494.

Figure 19:
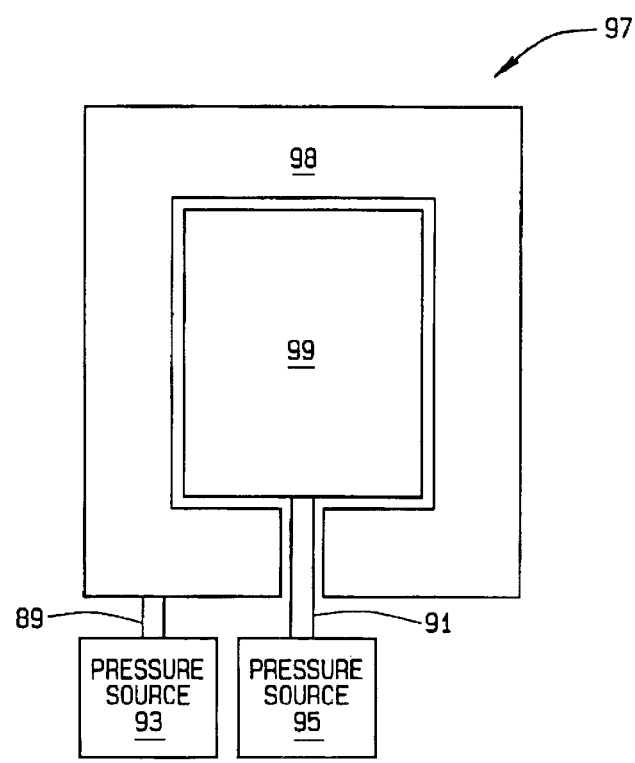
FIG. 19 is a plan view of the pressurization bladder shown in FIGS. 2A and 2B which may be used to apply pressure to the seal frame to seal the seal frame against the workpiece.

As shown in FIGS. 2 and 19, the apparatus 10 further includes a pressure bladder 97 positioned for developing pressure on the dies 14 and/or 16. In the particular illustrated embodiment, the pressure bladder 97 is positioned beneath the second die 16, with upwardly directed pressure being developed against the second die 16 when a pressurized fluid is received within the pressure bladder 97. Although a wide range of materials may be used, the pressure bladder 97 in an exemplary embodiment is formed from 0.060 inch (0.15 centimeter) gauge corrosion-resistant stainless steel.

The pressure bladder 97 includes a first pressure zone 98 and a second pressure zone 99. The first pressure zone 98 is in fluid communication with a source of pressurized fluid 93 via conduit 89 (e.g., stainless steel tube, etc.). The second pressure zone 99 is in fluid communication with a source of pressurized fluid 95 via conduit 91 (e.g., stainless steel tube, etc.). Pressure on the second die 16 can be developed by pressurizing either or both of the pressure zones 98 and 99.

The first pressure zone 98 is located underneath the peripheral portions 76 and 78 of the respective seal frame members 74 and 73 such that the upward pressure on the second die 16 (developed by pressurizing the first pressure zone 98) is concentrated on the seal frame peripheral portions 76 and 78. In one embodiment, pressure of about 2600 pounds per square inch (psi) on the seal frame peripheral portions 76 and 78 is developed by pressuring the first pressure zone 98 to about 162 psi.

To seal the seal frame assembly 44 against the workpiece 26, the pressure source 93 provides a pressurized fluid to the first pressure zone 98. The pressurized fluid within the first pressure zone 98 creates pressure on the second die 16. This pressure, in turn, causes the seal beads 75 on the seal frame peripheral portion 76 to be pressed into the workpiece 26 and also causes the seal frame peripheral portions 76 and 78 to abut or become flush against the dies 16 and 14, respectively. Alternatively, hydraulics can also used to provide the pressure against one or both of the dies 14 and 16 for sealing the seal frame assembly against the workpiece.

The second pressure zone 99 is located below the middle portion of the workpiece 26. The pressurization of the second pressure zone 99 by the pressure source 95 may be slaved to or dependent upon the part forming pressure within the pressurizing cavity 70. The pressure within the second pressure zone 99 may be ramped up or increased along with the part forming pressure. Additional pressure may also be applied to the first pressure zone 97 as the forming pressure in the cavity 70 is ramped up.

In the particular illustrated embodiments, the second die 16 defines a ridge 81. The first die 14 defines a relief 82 for receiving the ridge 81 therein when the first and second dies 14 and 16 are closed. Alternatively, the first die may include the ridge, and the second die may include the relief. In either case, the ridge may be either an integral part of the corresponding die or a separate component attached to the corresponding die.

The ridge 81 and the relief 82 are positioned external to the die cavity 25 and prevent the transfer of radiant heat from the hot tooling (e.g., workpiece 26, seal frame assembly 44, susceptor 42, etc.) through a gap or space 96 between the first and second dies 14 and 16 outwardly beyond the ridge 81 and the relief 82.

The second side 43 of the workpiece 26 is purged by the introduction of inert forming gas into the pressurizing cavity 70. To allow the first side 83 of the workpiece 26 to be purged with an inert gas and thus allow part surface contamination to be eliminated, or at least reduced, a fluidic sealing member 84 is positioned between the first and second dies 14 and 16 external to the die cavity 25. The fluidic sealing member 84 allows an inert atmosphere to be placed around the workpiece 26 during the forming operation and permits purging of the first side 83 of the workpiece 26 to withdraw volatiles and eliminate, or at least reduce, part surface contamination.

The thermally insulative ceramic dies 14 and 16 prevent conductive heat transfer to the fluidic sealing member 84. However, radiant heat transferring from the hot tooling (e.g., workpiece 26, seal frame assembly 44, susceptor 42, etc.) through the space 96 between the first and second dies 14 and 16 to the fluidic sealing member 84 can lead to degradation of the material (e.g., elastomer, etc.) from which the fluidic sealing member 84 is formed. By positioning the fluidic sealing member 84 outside of the ridge 81 and the relief 82, the ridge 81 and relief 82 effectively eliminate the line of sight from the hot tooling to the fluidic sealing member 84. In doing so, the ridge 81 and the relief 82 when engaged with one another eliminate, or at least reduce, the radiant heat transfer from the hot tooling to the fluidic sealing member 84.

A description of an exemplary operational sequence will now be provided for the induction heating workcell 10 shown in FIGS. 1 through 7. In this example, the apparatus 10 is employed for superplastic forming a single sheet workpiece 26, which may be a titanium, steel, or aluminum plate having stiffeners machined therein and/or welded thereon. Various embodiments of the invention may be used in other forming operations to form other materials besides titanium.

First, the workpiece 26 is loaded between the dies 14 and 16 when the dies 14 and 16 are separated. The dies 14 and 16 are then brought together, for example, by raising the lower die set 16 and the lower strongback 20 with one or more pneumatic actuators positioned beneath the lower strongback 20. Nuts 19 are then threaded upwards on the jackscrews 22 to hold the upper and lower strongbacks 18 and 20 together and to develop a clamping force having sufficient magnitude to facilitate the superplastic forming operation.

An inert atmosphere may be introduced into the die cavity 25 to protect the workpiece 26 from oxidization. The first pressure zone 98 of the pressure bladder 97 is pressurized to create the pressure for sealing the workpiece 26 against the seal frame assembly 44.

The coil driver and the coolant source are actuated to respectively provide the induction coil 36 with an alternative electric current and a coolant. In response to the electrical field provided by the coil driver, the induction coil 36 produces electromagnetic flux that is employed to inductively heat the susceptor 42. The susceptor 42 then transfers heat to the workpiece 26. The coolant that flows through the induction coil 36 removes excess heat from the induction coil 36.

After the workpiece 26 has been heated sufficiently to a temperature within its superplastic temperature forming range, an inert gas under sufficient pressure is introduced into the pressurizing cavity 70. The pressure within the second pressure zone 99 of the pressure bladder 97 is increased along with the part forming pressure within the cavity 70. Additional pressure may also be applied to the first pressure zone 97 as the forming pressure in the cavity 70 is ramped up.

The pressure in the compartment 70 is regulated to control the rate by which the workpiece 26 deforms. Due to the elevated temperature of the workpiece 26, the workpiece 26 is relatively ductile and readily deforms under the pressure of the gas within the cavity 70. The workpiece 26 is pushed into direct contact with the forming surface 23 of the first die 14. After the workpiece 26 has been formed, the power to the induction coil 36 is disengaged and the gas pressure within the pressurizing cavity 70 and the bladder pressure zones 98 and 99 is released. If desired, the flow of coolant through the induction coil 36 may be maintained while the workpiece 26 is allowed to cool. When the workpiece 26 has sufficiently cooled, the dies 14 and 16 are opened and the finished part is removed.

In at least some embodiments, the susceptor 42 is not formed along with the workpiece 26. The pressure within the cavity 70 deforms the workpiece 26 but not the susceptor 42. Accordingly, the susceptor 42 can be reused in subsequent operational sequences of the workcell 10 in which additional workpieces are formed.

In another form, the present invention provides a method for induction heating forming a workpiece. In one embodiment, the method comprises: positioning the workpiece within a die cavity defined by a pair of dies; producing an oscillating magnetic field within the die cavity to induce a current within a susceptor to heat the susceptor, the susceptor being positioned within the die cavity between the workpiece and one die surface defined by one of the dies, the one die surface cooperating with a forming surface defined by the other one of the dies to define the die cavity; transferring heat from the susceptor to the workpiece; and forming the workpiece into direct contact with the forming surface when the workpiece reaches a forming temperature.

The method may further include releasably engaging the workpiece with a seal frame assembly to form a pressurizing cavity between the seal frame and the one side of the workpiece; and injecting a pressurized forming fluid into the pressurizing cavity to apply pressure to the workpiece to deform the workpiece against the forming surface. The forming temperature at which the workpiece is formed may be within a superplastic temperature forming range within which the workpiece has superplastic properties. In addition, the method may further include electrically connecting the susceptor to the workpiece; actively cooling the electrical connection between the susceptor and the workpiece; and/or providing an electrically nonconductive material between the susceptor and the workpiece.

The method may also include engaging a ridge defined by one of the dies external to the die cavity with a relief defined by the other one of the dies to inhibit heat that is radiantly transferring through a gap between the dies from transferring outwardly beyond the ridge and the relief.

It is anticipated that the invention will be applicable to any of a wide range of forming processes including hot forming, superplastic forming, thermoforming, consolidation, heat treatment, etc. Accordingly, the specific references to a specific type of forming process herein should not be construed as limiting the scope of the present invention to only that specific type of forming process.

The description of the invention is merely exemplary in nature and is in no way intended to limit the invention, its application, or uses. Thus, variations that do not depart from the substance of the invention are intended to be within the scope of the invention. Such variations are not to be regarded as a departure from the spirit and scope of the invention.

What is claimed is:

1. An induction heating apparatus for forming sheet products, the induction heating apparatus comprising:
   a pair of dies defining a die cavity for containing a product;
   a susceptor between the product and one die surface defined by one of the dies, the one die surface cooperating with a forming surface defined by the other one of the dies to define the die cavity;
   an induction heater to induce eddy currents in the susceptor to heat the susceptor, the susceptor transferring heat to the product; and
   an inlet for pressurized forming fluid to inject the fluid between the susceptor and the product to form the product into direct contact with the forming surface.

2. The apparatus of claim 1, further comprising an electrically nonconductive matenal between the product and the susceptor.

3. The apparatus of claim 1, wherein the susceptor is electrically connected to the product to enable current to flow from the susceptor to the product and from the product to the susceptor.

4. The apparatus of claim 3, further comprising at least one cooling passage for the delivery of coolant adjacent an electrical connection between the susceptor and the product.

5. The apparatus of claim 1, further comprising a seal frame for releasably engaging the product to form a pressurizing cavity between the product and the seal frame, the inlet injecting the fluid into the pressurizing cavity to develop and apply forming pressure to the product.

6. The apparatus of claim 5, further comprising at least one seal bead on the seal frame, the seal bead being releasably pressed into the product to fluidically seal the pressurizing cavity.

7. The apparatus of claim 6, further comprising a pressure bladder adjacent one of the dies, the pressure bladder receiving a pressurized fluid therein to develop and apply pressure to the seal frame for causing the seal bead to be pressed into the product.

8. The apparatus of claim 5, wherein the seal frame includes:
   a first seal frame member between the product and the forming surface;
   a second seal frame member between the product and the susceptor; and
   the first and second seal frame members releasably engaging the product therebetween to form the pressurizing cavity between the product and the second seal frame member.

9. The apparatus of claim 1, wherein the forming surface includes a die liner formed of a material not susceptible to inductive heating, and wherein the product is formed into direct contact with the die liner along the forming surface.

10. The apparatus of claim 1, further comprising:
   a ridge defined by one of the dies external to the die cavity;
   a relief defined by the other one of the dies to receive the ridge therein when the dies are closed; and
   the ridge and relief, when engaged with one another, inhibiting heat that is radiantly transferring through a gap between the dies from transferring outwardly beyond the ridge and the relief.

11. The apparatus of claim 10, further comprising a fluidic sealing member positioned between the dies external to the ridge and the relief.

12. An induction heating apparatus for forming sheet products, the induction heating apparatus comprising:
   a pair of dies defining a die cavity for containing a product to be inductively heated by an oscillating magnetic field within the die cavity;
   a first seal frame member between the product and a forming surface defined by one of the dies;
   a second seal frame member between the product and one die surface defined by the other one of the dies, the one die surface cooperating with the forming surface to define the die cavity;
   the first and second seal frame members releasably engaging the product therebetween to form a pressurizing cavity between the product and the second seal frame member; and
   an inlet for pressurized forming fluid to inject the fluid into the pressurizing cavity to form the product into the forming surface.

13. The apparatus of claim 12, further comprising at least one seal bead on at least one of the first and second seal frame members, the seal bead being releasably pressable into the product for fluidically sealing the pressurizing cavity.

14. The apparatus of claim 13, further comprising a pressure bladder adjacent one of the dies, the pressure bladder receiving a pressurized fluid therein to develop and apply pressure for causing the seal bead to be pressed into the product.

15. The apparatus of claim 14, wherein the first and second seal frame members include tapered peripheral portions sized to be received within correspondingly tapered recesses within the dies.

16. The apparatus of claim 12, wherein the product is formed into direct contact with the forming surface.

17. The apparatus of claim 12, further comprising at least one susceptor capable of coupling with the oscillating magnetic field to create a current within the susceptor to heat the susceptor, the susceptor transferring heat to the product.

18. The apparatus of claim 17, wherein the susceptor is between the second seal frame member and the one die surface.

19. The apparatus of claim 17, further comprising an electrically nonconductive material between the susceptor and the product.

20. The apparatus of claim 17, wherein the susceptor is electrically connected to the product to enable current to flow from the susceptor to the product and from the product to the susceptor.

21. The apparatus of claim 20, further comprising at least one cooling passage for the delivery of coolant adjacent an electrical connection between the susceptor and the product.

22. The apparatus of claim 20, wherein at least one of the first and second seal frame members electrically connects the product and the susceptor.

23. The apparatus of claim 12, further comprising:
   a ridge defined by one of the dies external to the die cavity;
   a relief defined by the other one of the dies to receive the ridge therein when the dies are closed; and
   the ridge and relief, when engaged with one another, inhibiting heat that is radiantly transferring through a gap between the dies from transferring outwardly beyond the ridge and the relief.

24. The apparatus of claim 23, further comprising a fluidic sealing member positioned between the dies external to the ridge and the relief.

25. A seal frame assembly comprising:
   a first seal frame member adjacent a forming surface defined by one of a pair of dies;
   a second seal frame member adjacent one die surface defined by the other one of the dies, the one die surface cooperating with the forming surface to define a die cavity for containing a workpiece;
   the first and second seal frame members releasably engaging a workpiece therebetween to form a pressurizing cavity between the workpiece and the second seal frame member; and
   an inlet for pressurized forming fluid to inject the fluid into the pressurizing cavity to form the product into the forming surface.

26. The seal frame assembly of claim 25, further comprising at least one seal bead on at least one of the first and second seal frame members, and wherein the pressurizing cavity being fluidically sealed when the seal bead is releasably pressed into the workpiece.

27. The seal frame assembly of claim 25, wherein the first and second frame members include tapered peripheral portions sized to be received within correspondingly tapered recesses within the dies.

28. A method for induction heating forming a nonmagnetic workpiece, the method comprising:
   positioning the workpiece within a die cavity defined by a pair of dies;
   producing an oscillating magnetic field within the die cavity to induce a current within a susceptor to heat the susceptor, the susceptor being positioned within the die cavity between the workpiece and one die surface defined by one of the dies, the one die surface cooperating with a forming surface defined by the other one of the dies to define the die cavity;
   transferring heat from the susceptor to the workpiece; and
   forming the workpiece into direct contact with the forming surface when the workpiece reaches a forming temperature.

29. The method of claim 28, wherein forming the workpiece comprise injecting pressurized forming fluid between the susceptor and the workpiece.

30. The method of claim 29, wherein injecting pressurized forming fluid between the susceptor and the workpiece comprises:
   releasably engaging the workpiece with a seal frame to form a pressurizing cavity between the workpiece and the seal frame; and
   injecting the pressurized forming fluid into the pressurizing cavity.

31. The method of claim 30, wherein releasably engaging the workpiece with a seal frame comprises pressurizing a pressure bladder adjacent one of the dies to create a pressure for pressing a seal bead on the seal frame into the workpiece.

32. The method of claim 28, further comprising electrically connecting the susceptor and the workpiece.

33. The method of claim 32, further comprising actively cooling an electrical connection between the susceptor and the workpiece.

34. The method of claim 28, further comprising engaging a ridge defined by one of the dies external to the die cavity with a relief defined by the other one of the dies to inhibit heat that is radiantly transferring through a gap between the dies from transferring outwardly beyond the ridge and the relief.

35. The method of claim 28, further comprising providing an electrically nonconductive material between the susceptor and the workpiece.

36. The method of claim 28, wherein the susceptor is not formed along with the workpiece.

37. The method of claim 28, further comprising reusing the susceptor for induction heating forming a second workpiece.

38. The method of claim 29, wherein injecting pressurized forming fluid creates a driving pressure between the susceptor and the workpiece for forming the workpiece, and wherein the susceptor is not formed by the driving pressure.

39. The method of claim 38, further comprising reusing the susceptor for induction heating forming a second workpiece.

* * * * *